US011122997B2

(12) United States Patent
Ray et al.

(10) Patent No.: US 11,122,997 B2
(45) Date of Patent: Sep. 21, 2021

(54) MODULATING THE ARYL HYDROCARBON RECEPTOR SYSTEM TO TREAT MAJOR DEPRESSIVE DISORDER

(71) Applicants: Mayo Foundation for Medical Education and Research, Rochester, MN (US); Ixcela Inc., Bedford, MA (US); Duke University, Durham, NC (US)

(72) Inventors: Balmiki Ray, Rochester, MN (US); Liewei Wang, Rochester, MN (US); Joanna Biernacka, Rochester, MN (US); Mark Frye, Rochester, MN (US); Richard M. Weinshilboum, Rochester, MN (US); Michiaki Kubo, Kanagawa (JP); Taisei Mushiroda, Kawaguchi (JP); Wayne R. Matson, Ayer, MA (US); Rima Kaddurah-Daouk, Belmont, MA (US)

(73) Assignees: Mayo Foundation for Medical Education and Research, Rochester, MN (US); Ixcela Inc., Bedford, MA (US); Duke University, Durham, NC (US)

( * ) Notice: Subject to any disclaimer, the term of this patent is extended or adjusted under 35 U.S.C. 154(b) by 494 days.

(21) Appl. No.: 15/567,176

(22) PCT Filed: Apr. 15, 2016

(86) PCT No.: PCT/US2016/027879
§ 371 (c)(1),
(2) Date: Oct. 17, 2017

(87) PCT Pub. No.: WO2016/168685
PCT Pub. Date: Oct. 20, 2016

(65) Prior Publication Data
US 2018/0098722 A1    Apr. 12, 2018

Related U.S. Application Data

(60) Provisional application No. 62/149,285, filed on Apr. 17, 2015.

(51) Int. Cl.
| | | |
|---|---|---|
| *A61K 31/12* | (2006.01) | |
| *A61B 5/145* | (2006.01) | |
| *A61B 5/16* | (2006.01) | |
| *A61B 5/00* | (2006.01) | |
| *G01N 33/68* | (2006.01) | |
| *A61K 31/015* | (2006.01) | |
| *A61K 31/404* | (2006.01) | |
| *A61K 31/05* | (2006.01) | |
| *A61K 31/352* | (2006.01) | |
| *A61K 31/00* | (2006.01) | |

(52) U.S. Cl.
CPC ......... *A61B 5/14546* (2013.01); *A61B 5/165* (2013.01); *A61B 5/4839* (2013.01); *A61K 31/00* (2013.01); *A61K 31/015* (2013.01); *A61K 31/05* (2013.01); *A61K 31/12* (2013.01); *A61K 31/352* (2013.01); *A61K 31/404* (2013.01); *G01N 33/6872* (2013.01); *G01N 2500/10* (2013.01)

(58) Field of Classification Search
CPC combination set(s) only.
See application file for complete search history.

(56) References Cited

U.S. PATENT DOCUMENTS

| | | | |
|---|---|---|---|
| 6,432,692 B1 | 8/2002 | Bradfield et al. | |
| 8,546,342 B2 * | 10/2013 | Lines | A23L 2/52 514/27 |
| 9,757,378 B2 * | 9/2017 | Sauvageau | A61K 31/522 |
| 2006/0257405 A1 | 11/2006 | Golz et al. | |
| 2008/0102467 A1 | 5/2008 | McMahon et al. | |
| 2012/0225833 A1 | 9/2012 | Lines | |
| 2012/0252896 A1 | 10/2012 | Ernst et al. | |

FOREIGN PATENT DOCUMENTS

WO    WO 2013/074676    5/2013

OTHER PUBLICATIONS

Abdallah et al., "Ketamine and rapid-acting antidepressants: a window into a new neurobiology for mood disorder therapeutics," *Annual Rev Med.*, 66:509-523, 2015.
Abramoff et al., "Image processing with ImageJ," *Biophotonics Intl.*, 11(7):36-42, 2004.
Coplan et al., "A Neurobiological Hypothesis of Treatment-Resistant Depression—Mechanisms for Selective Serotonin Reuptake Inhibitor Non-Efficacy," *Front Behav Neurosci.*, 8:189, 2014.
Drewniany et al., "Rapid-onset antidepressant action of ketamine: potential revolution in understanding and future pharmacologic treatment of depression," *J Clin Pharm Ther.*, 40(2):125-130, Apr. 2015.
Driesen et al., "Relationship of Resting Brain Hyperconnectivity and Schizophrenia-like Symptoms Produced by the NMDA receptor Antagonist Ketamine in Humans," *Mol Psych.*, 18(11):1199-1204, 2013.
Ellsworth et al., "FKBP5 genetic variation: association with selective serotonin reuptake inhibitor treatment outcomes in major depressive disorder," *Pharmacogenet Genom.*, 23(3):1S6-166, 2013.
Ferrari et al., "Burden of Depressive Disorders by Country, Sex, Age, and Year: Findings from the Global Burden of Disease Study 2010," *PLOS Medicine.*, 10(11):e1001547, 2013.
Frye, "Bipolar Disorder—A Focus on Depression," *N Engl J Med.*, 364(1):51-59, Jan. 6, 2011.

(Continued)

*Primary Examiner* — Heidi Reese
(74) *Attorney, Agent, or Firm* — Fish & Richardson P.C.

(57) ABSTRACT

Materials and methods for treating major depressive disorder by modulating the aryl hydrocarbon receptor system are provided herein.

6 Claims, 22 Drawing Sheets

(56) References Cited

OTHER PUBLICATIONS

Haarmann-Stemmann et al., "Analysis of the Transcriptional Regulation and Molecular Function of the Aryl Hydrocarbon Receptor Repressor in Human Cell Lines," *Drug Metab Dispos.*, 35(12):2262-2269, Dec. 1, 2007.

Haase and Brown, "Integrating the monoamine, neurotrophin and cytokine hypotheses of depression—a central role for the serotonin transporter?," *Pharmacol Ther.*, 147:1-11, Mar. 2015.

Henry et al., "A potential endogenous ligand for the aryl hydrocarbon receptor has potent agonist activity in vitro and in vivo," *Arch Biochem Biophys.*, 450(1):67-77, 2006.

Ingle et al., "Selective estrogen receptor modulators and pharmacogenomic variation in ZNF423 regulation of BRCA1 expression: Individualized breast cancer prevention," *Cancer Discovery.*, 3(7):812-825, Jul. 2013.

International Preliminary Report on Patentability in International Application No. PCT/US2016/027879, dated Oct. 17, 2017, 7 pages.

International Search Report and Written Opinion in International Application No. PCT/US2016/027879, dated Jul. 15, 2016, 9 pages.

Ionescu et al., "A single infusion of ketamine improves depression scores in patients with anxious bipolar depression," *Bipolar Disord.*, 17 (4): 438-443, 2014.

Ji et al., "Glycine and a Glycine Dehydrogenase (GLDC) SNP as Citalopram/Escitalopram Response Biomarkers in Depression: Pharmacometabolomics-Informed Pharmacogenomics," *Clin Pharmacol Ther.*, 89(1):97-104, 2011.

Ji et al., "Pharmacogenomics of selective serotonin reuptake inhibitor treatment for major depressive disorder: genome-wide associations and functional genomics," *Pharmacogenomics J.*, 13(5):456-463, Oct. 2013.

Karchner et al., "Regulatory Interactions among Three Members of the Vertebrate Aryl Hydrocarbon Receptor Family: AHR Repressor, AHR1, and AHR2," *J Biol Chem.*, 277(9):6949-2959, 2002.

Mimura and Fujii-Kuriyama, "Functional role of AhR in the expression of toxic effects by TCDD," *Biochim Biophys Acta.*, 1619(3):263-268, 2003.

Nebert et al., "Role of aryl hydrocarbon receptor-mediated induction of the CYP1 enzymes in environmental toxicity and cancer," *J Biol Chem.*, 279(23):23847-23850, Jun. 4, 2004.

Nguyen., "The search for endogenous activators of the aryl hydrocarbon receptor," *Chem Res Toxicol.*, 21(1):102-116, Jan. 2008.

Niu et al., "Radiation pharmacogenomics: A genome-wide association approach to identify radiation response biomarkers using human lymphoblastoid cell lines," *Genome Res.*, 20(11):1482-1492, 2010.

Oxenkrug, "Serotonin-kynurenine hypothesis of depression: historical overview and recent developments," *Curr Drug Targets.*, 14(5):514-521, May 1, 2013.

Trivedi et al., "Evaluation of outcomes with citalopram for depression using measurement-based care in STAR*D: implications for clinical practice," *Am J Psych.*, 163(1 ):28-40, Jan. 2006.

Van Zoonen et al., "Preventing the onset of major depressive disorder: a meta-analytic review of psychological interventions," *Int J Epidemiol.*, 43(2):318-329, Apr. 2014.

\* cited by examiner

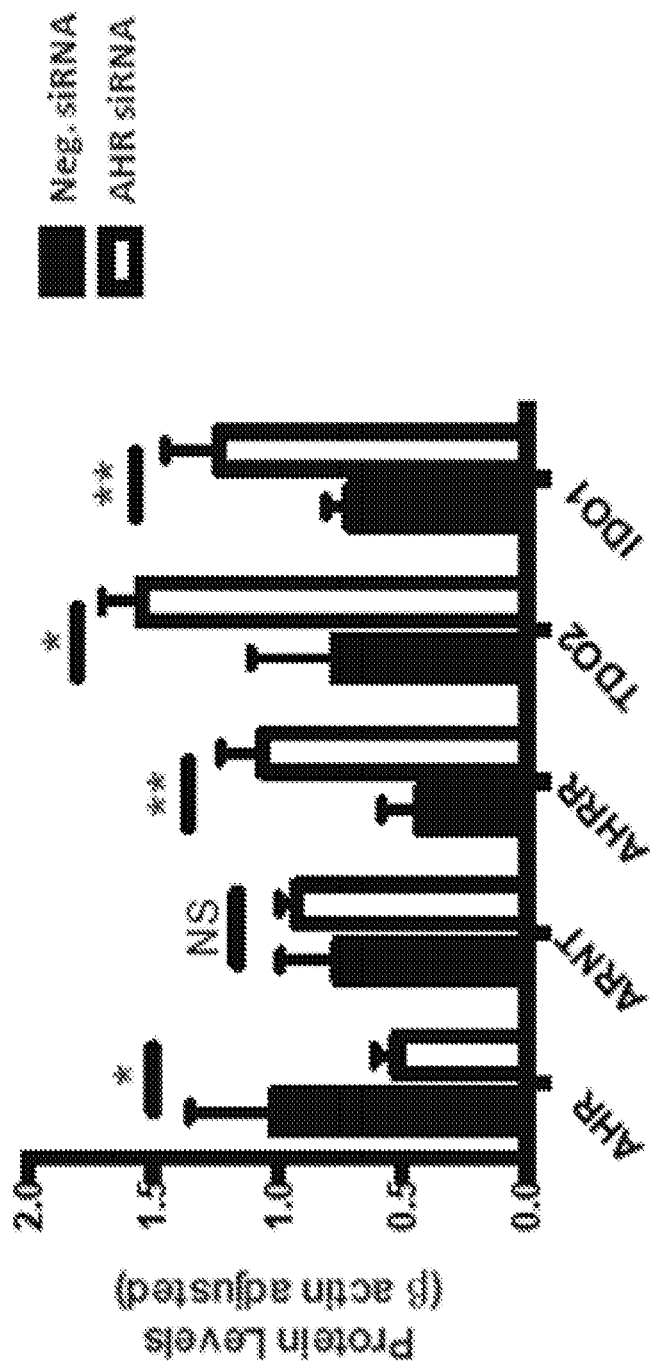

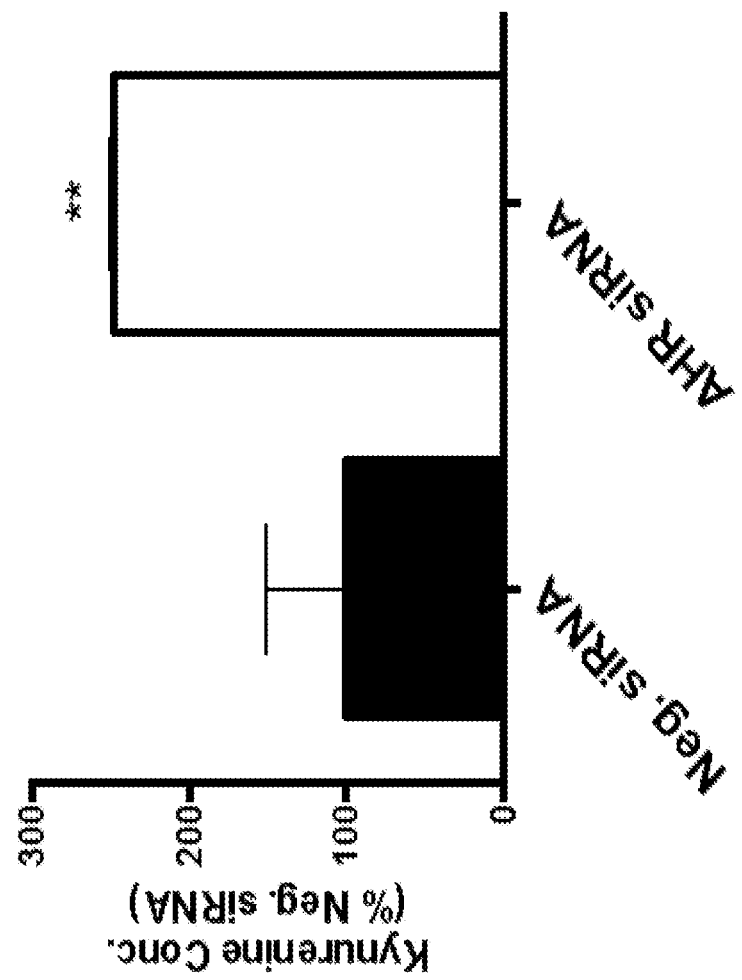

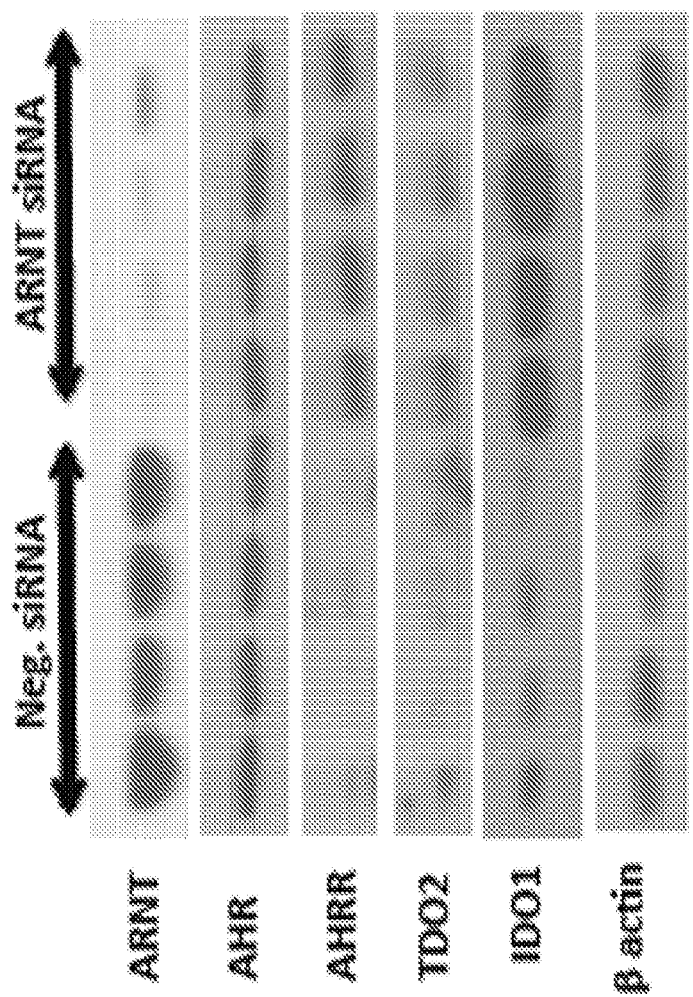

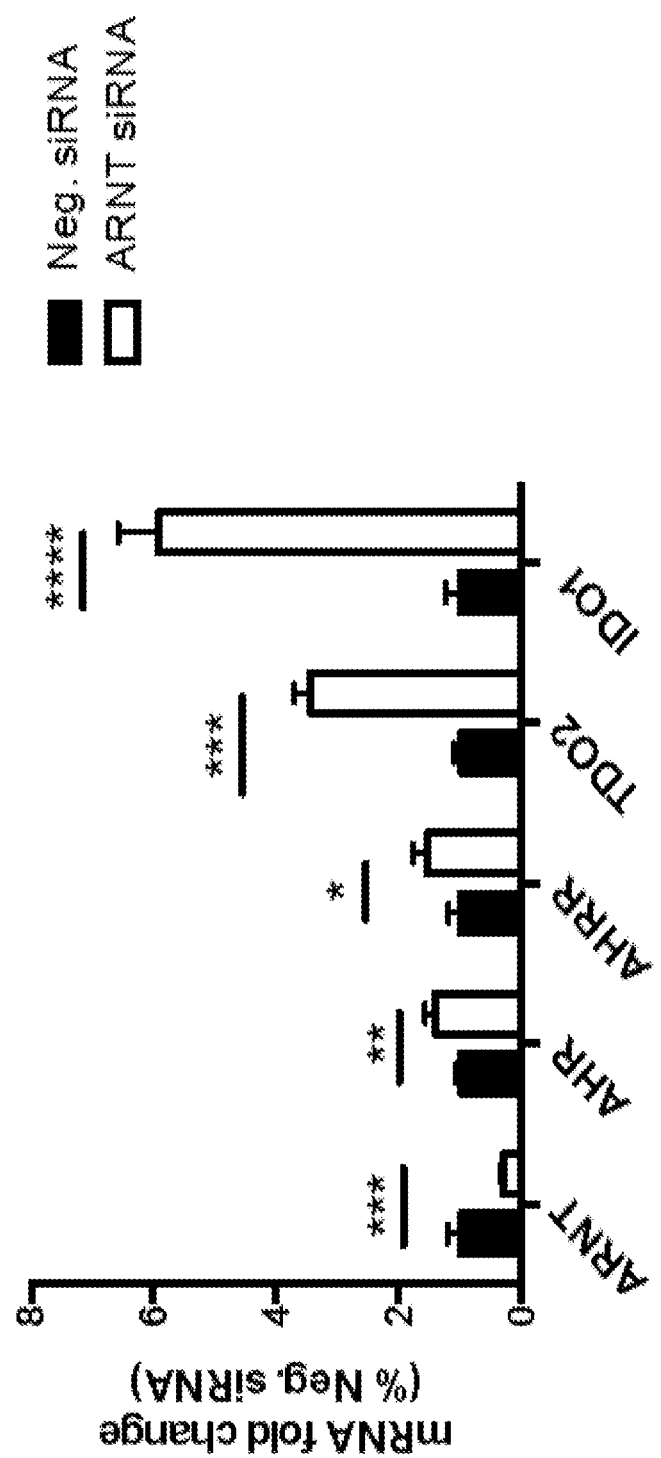

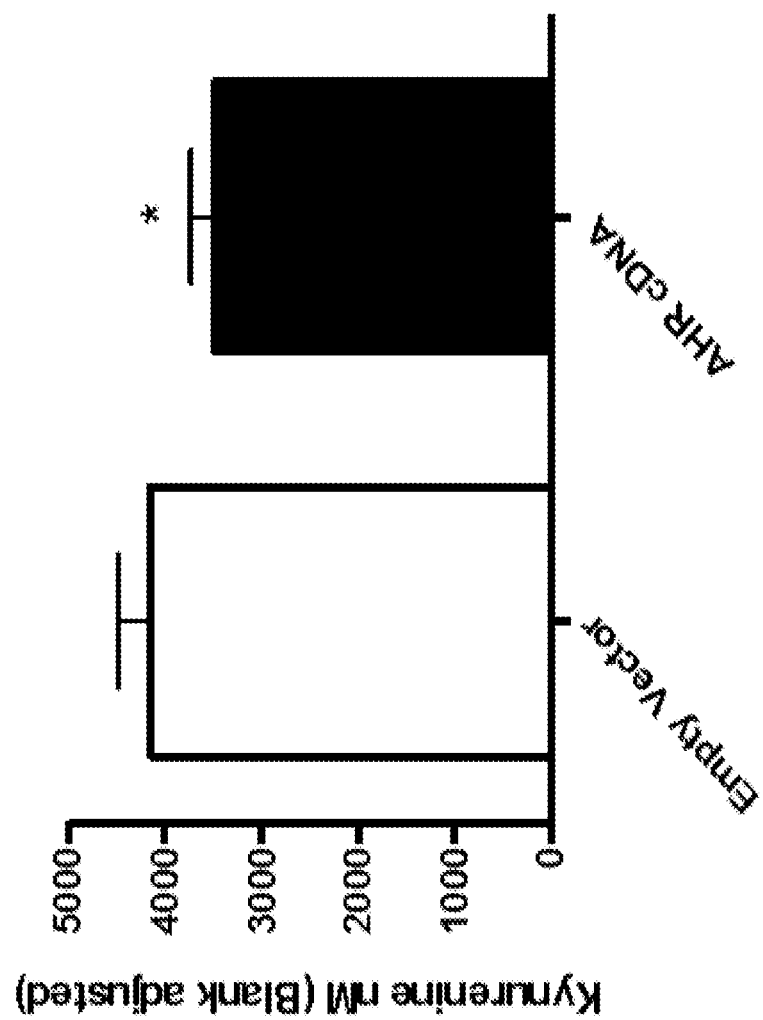

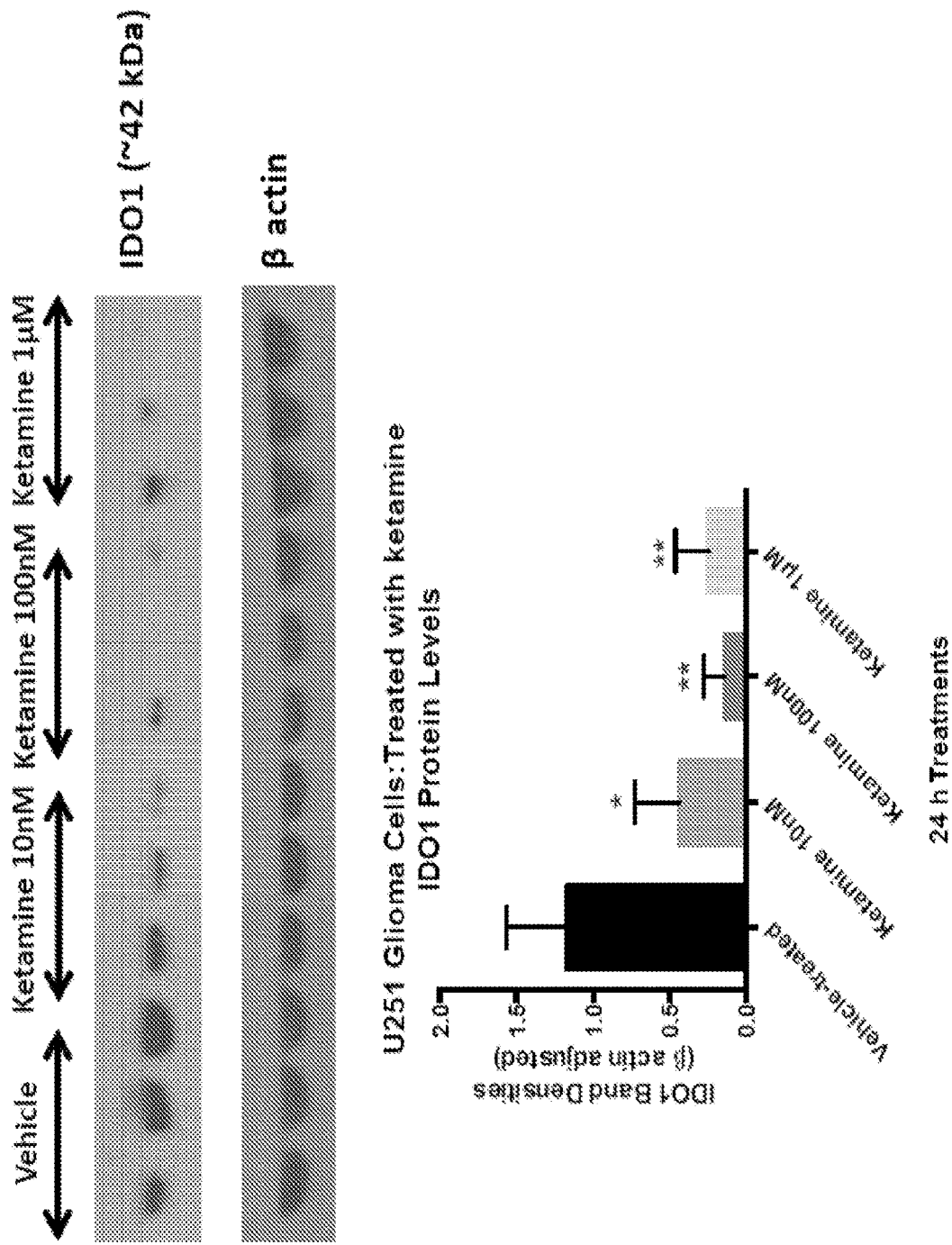

MODULATING THE ARYL HYDROCARBON RECEPTOR SYSTEM TO TREAT MAJOR DEPRESSIVE DISORDER

CROSS-REFERENCE TO RELATED APPLICATIONS

This application is a National Stage application under 35 U.S.C. §371 of International Application No. PCT/US2016/027879, having an International Filing Date of Apr. 15, 2016, which claims benefit of priority from U.S. Provisional Application Ser. No. 62/149,285, filed on Apr. 17, 2015. This disclosure of the prior applications are considered part of (and are incorporated by reference in) the disclosure of this application.

STATEMENT AS TO FEDERALLY SPONSORED RESEARCH

This invention was made with government support under GM028157 and GM061388, awarded by the National Institutes of Health. The government has certain rights in the invention.

TECHNICAL FIELD

This document relates to materials and methods for treating a depression disorder (e.g., major depressive disorder, or a major depressive episode associated with bipolar disorder), and more particularly to materials and methods for treating major depressive disorder using agents that activate the aryl hydrocarbon receptor, without interacting with the glutamate receptor.

BACKGROUND

Major Depressive Disorder (MDD) is the most common psychiatric disorder psychiatric disease worldwide, and is estimated to affect more than 150 million people around the globe (van Zoonen et al., *International Journal Epidemiol* 43(2):318-329, 2014; and Ferrari et al., *PLoS Medicine* 10(11):e1001547, 2013). Dysregulation in the function of the monoamine neurotransmitter systems is thought to be associated with the pathogenesis of MDD (Haase and Brown, *Pharmacol Ther* 147C:1-11, 2015). The drugs most commonly used to treat MDD are the selective serotonin re-uptake inhibitors (SSRIs) (Coplan et al., *Frontiers Behavioral Neurosci* 8:189, 2014), which prevent reuptake of serotonin (5HT) by pre-synaptic nerve terminals, resulting in increased concentrations of 5HT in synapses. However, only about half of MDD patients respond to SSRI therapy, with only about 32% of MDD patients achieving complete remission after 14 weeks of SSRI therapy (Trivedi et al., *Am J Psych* 163(1):28-40, 2006). Further, the response to SSRI treatment may be delayed for weeks or months, resulting in non-compliance to therapy. In addition, a meta-analysis comparing acute antidepressant treatment with either placebo or active comparator for major depression associated with bipolar disorder demonstrated no significant benefit of antidepressant therapy (Frye, *N Engl J Med* 364(1):51-59, 2011).

SUMMARY

This document is based at least in part on the discovery that the aryl hydrocarbon receptor (AHR) system plays a role in both the pathogenesis of MDD and the action of ketamine for treating MDD. This document also is based at least in part on the discovery that agonists of AHR may be useful therapeutic agents for treating MDD, and particular AHR agonists that do not interact with glutamate receptors.

In one aspect, this document features a method of screening for a compound that is an agonist of the AHR system but does not bind to a glutamate receptor. The method can include (a) performing an assay to determine whether the compound activates the AHR system; and (b) performing an assay to determine whether the compound interacts with the glutamate receptor. In step (a), the assay can include assessing the expression level of the AHR, AHR Repressor (AHRR), or AHR Nuclear Transporter (ARNT). The glutamate receptor can be the N-methyl-D-aspartate (NMDA) receptor. In step (b), the assay can include co-immunoprecipitation, or assessing the level of kynurenine.

In another aspect, this document features a method of identifying a candidate compound as being potentially useful for treating a depressive disorder. The method can include (a) performing an assay to determine that the candidate compound activates the AHR system; and (b) performing an assay to determine that the candidate compound does not interact with the glutamate receptor. The depression disorder can be MDD. In step (a), the assay can include assessing the expression level of AHR, AHRR, or ARNT. The glutamate receptor can be the NMDA receptor. In step (b), the assay can include co-immunoprecipitation or assessing the level of kynurenine.

This document also features a compound identified using a screening or identification method as described herein.

In another aspect, this document features a pharmaceutical composition containing a pharmaceutically acceptable carrier and a compound that is an AHR receptor agonist, and that does not bind to a glutamate receptor. Administration of the compound to a cell can result in increased levels of AHR and/or ARNT in the cell, decreased levels of AHRR in the cell, or both increased levels of AHR and/or ARNT and decreased levels of AHRR in the cell. The compound can be selected from the group consisting of 3-methyl cholanthrene, dioxin, 3',4'-dimethoxy-α-naphthoflavone (DiMNF), 3,3'-Diindolylmethane (DIM), resveratrol, and curcumin.

In yet another aspect, this document features a method for treating a depression disorder in a subject. The method can include administering to the subject a composition containing a pharmaceutically acceptable carrier and a compound that is an AHR receptor agonist, and that does not bind to a glutamate receptor. The depression disorder can be MDD. Administration of the composition to a cell can result in increased levels of AHR and/or ARNT in the cell, decreased levels of AHRR in the cell, or both increased levels of AHR and/or ARNT and decreased levels of AHRR in the cell. The glutamate receptor can be the NMDA receptor.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the descrip-

DESCRIPTION OF DRAWINGS

FIG. 5B is a graph plotting β-actin-adjusted protein levels for AHR, ARNT, AHRR, TDO2, and IDO1, as determined from the Western blot shown in FIG. 5A. n=4; *p<0.05; **p<0.01; NS, not significant.

FIG. 5D is a graph plotting the concentration of kynurenine secreted by U251 glioma cells treated with control or AHR siRNA. n=4; **p<0.01.

FIG. 6A is a picture of a Western blot showing levels of ARNT, AHR, AHRR, TDO2, IDO1, and β-actin in U251 glioblastoma cells after treatment of the cells with control or ARNT siRNA.

FIG. 6C is a graph plotting mRNA levels for ARNT, AHR, AHRR, TDO2, and IDO1 in U251 glioma cells after treatment of the cells with control or ARNT siRNA. n=4; *p<0.05; p<0.01; *p<0.001; ****p<0.0001.

FIG. 7C is a graph plotting the concentration of kynurenine secreted by U251 glioma cells treated with control or cas9 AHRR for clustered regularly interspaced short palindromic repeat- (CRISPR-) mediated AHRR knockdown. n=4; *p<0.05.

FIG. 9A (top panel) is a picture of a Western blot showing IDO1 protein or β-actin control in lysates of U251 glioma cells after treatment of the cells with vehicle or the indicated concentrations of ketamine for 24 hours. Relative band densities are plotted in the graph in the bottom panel of FIG. 9A.

DETAILED DESCRIPTION

Drug therapies for MDD, such as SSRIs, are limited in that only about half of MDD patients respond to therapy, and the response treatment may be greatly delayed. Ketamine, a rapid acting anesthetic agent, has been shown to rapidly reverse the symptoms of MDD in some patients, an effect that presumably is mediated by N-methyl-D-aspartate (NMDA) glutamate receptor antagonism.

Ketamine typically is used as an anesthetic agent in animals and children. Ketamine has been tested experimentally in MDD patients (Abdallah et al., *Annual Rev Med* 66:509-523, 2015), with encouraging results. Ketamine can cause rapid improvement in mood for severely depressed patients (Drewniany et al., *J Clin Pharm Ther* 40(2):125-130, 2015 (published online 26 Dec. 2014, DOI: 10.1111/jcpt.12238)). Further, a single infusion of ketamine may have effects that last for weeks (Ionescu et al., *Bipolar Disorders* 17(1):22-23, 2015 (published online 23 Oct. 2014, DOI: 10.1111/bdi.12264)). The antidepressant effect of ketamine appears to be primarily due to its ability to antagonize NMDA glutamate receptors (Driesen et al., *Mol Psych* 18(11):1199-1204, 2013). However, other NMDA receptor antagonists (e.g., memantine and MK801) fail to demonstrate ketamine-like antidepressant effects, indicating possible novel mechanisms of ketamine action in ameliorating depressive symptoms.

As described herein, the response to ketamine therapy has been related to genetic variation in the aryl hydrocarbon receptor (AHR) system. Ketamine has a profound effect on the AHR system, and the AHR system in turn influences ketamine response. This discovery has opened the way to novel targets for new drugs that could be used to treat MDD. Thus, this document relates to, inter alia, potential biomarkers and drugs for MDD, and to methods for treatment of MDD by activating the AHR system.

Figure 1:
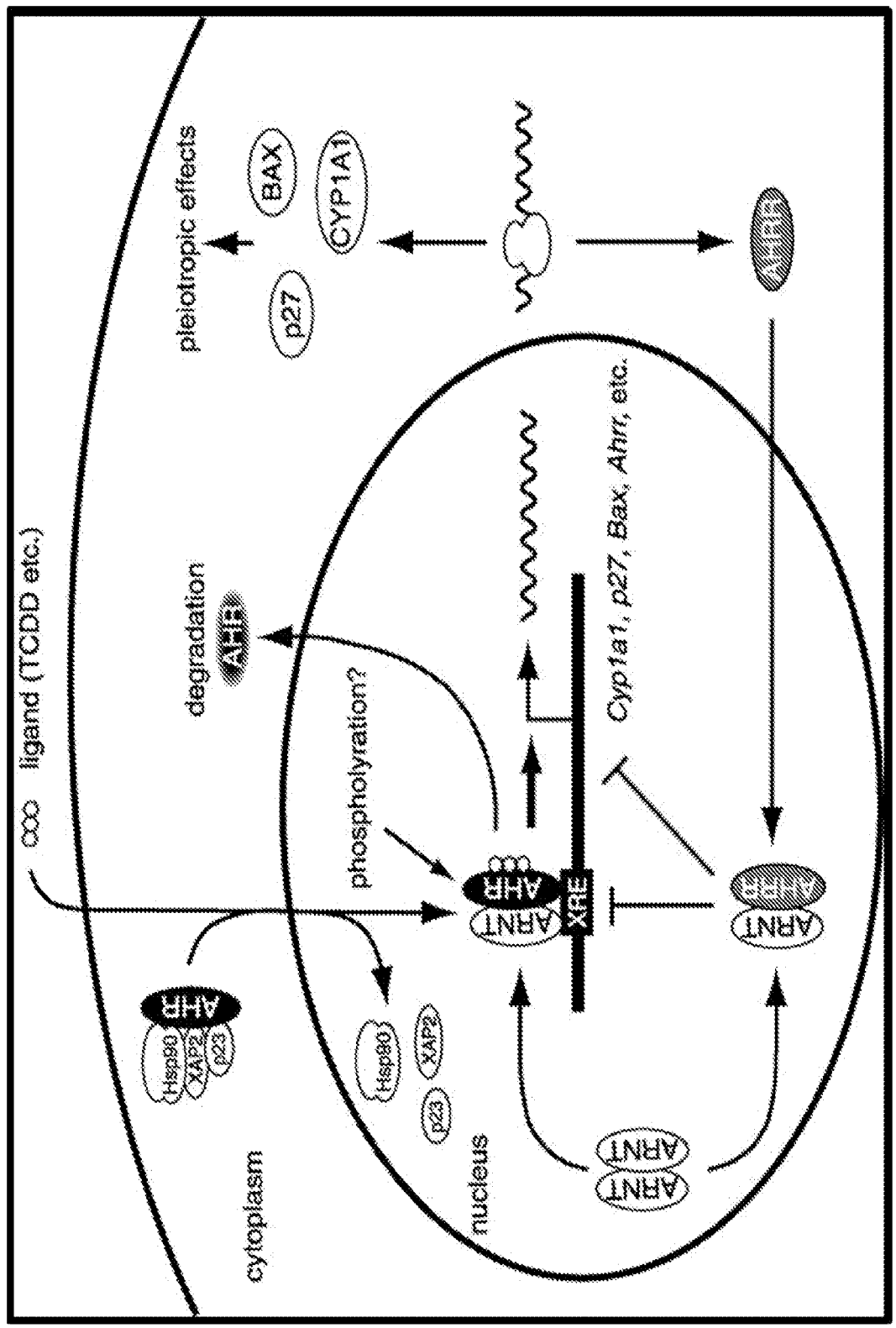
FIG. 1 is a diagram depicting the regulation of gene expression by AHR, AHR repressor (AHRR), and AHR nuclear transporter (ARNT) (Mimura and Fujii-Kuriyama, *Biochim Biophys Acta* 1619(3):263-268, 2003).

AHR is a basic helix-loop-helix/PAS domain containing ligand-activated transcription factor that, once activated, can bind to specific DNA motif sequences (called xenobiotic response elements or XREs) and initiate transcription (FIG. 1; see, also, Nebert et al., *J Biol Chem* 279(23):23847-23850, 2004). In the nucleus, AHR forms a heterodimer with another basic helix/PAS domain containing protein, AH Receptor Nuclear Transporter (ARNT) (Henry et al., *Arch Biochem Biophys* 450(1):67-77, 2006), and the AHR/ARNT heterodimer is thought to bind to XRE sequences. However, AHR Repressor (AHRR) competes with AHR to bind with ARNT, and represses AHR functions (FIG. 1; see, also, Karchner et al., *J Biol Chem* 277(9):6949-2959, 2002).

Figure 2:
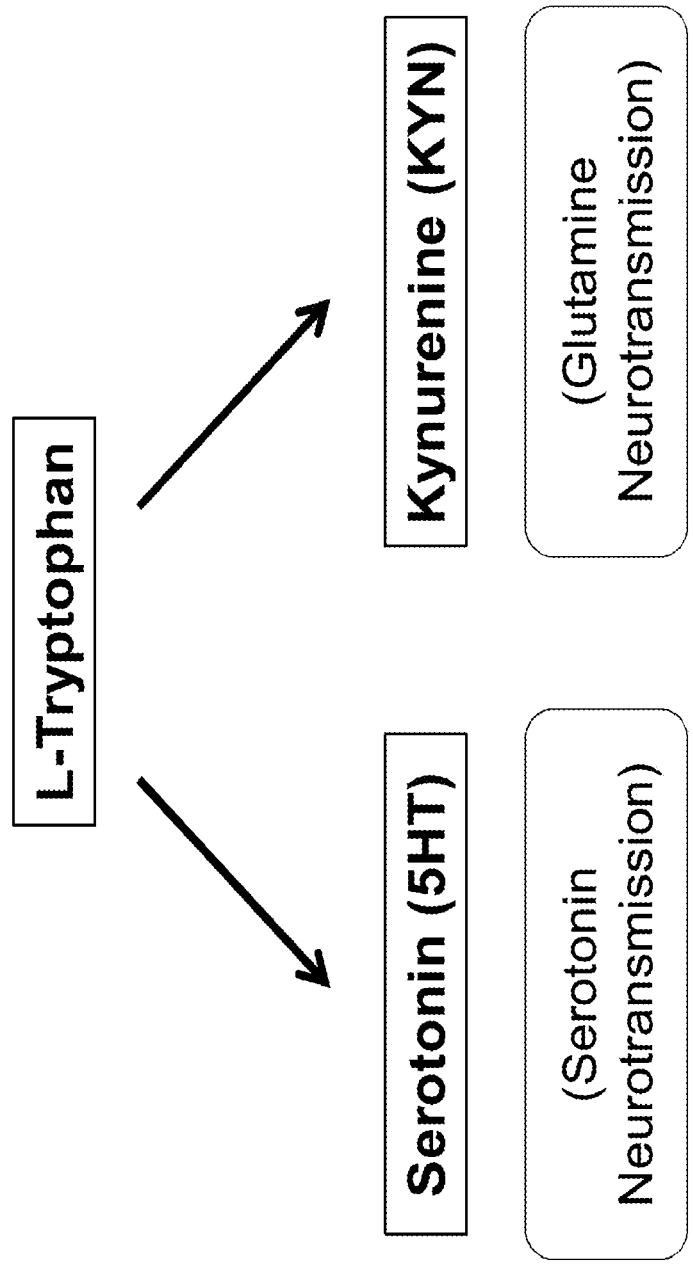
FIG. 2 is a diagram depicting the serotonin-kynurenine balance.

Kynurenine (KYN) pathway metabolites also are thought to be important in the pathogenesis of psychiatric disorders such as MDD (Oxenkrug, *Curr Drug Targets* 14(5):514-521, 2013). 5HT and KYN are both metabolites of tryptophan (TRP), an amino acid that is converted to 5HT by the enzymatic action of tryptophan hydroxylase (TPH) 1 and 2, but also is converted to KYN enzymatically by IDO1, indolamine 2,3 dioxygenase 2 (IDO2), and TDO2. See, FIG. 2. The majority of the TRP is metabolized to form KYN, and relatively smaller amounts are used to generate 5HT. The KYN pathway and the balance between 5HT and KYN are believed to be important in the pathogenesis and drug response in MDD. For example, a minor increase in KYN production can drastically reduce the amount of available TRP to generate 5HT. In addition, a downstream metabolite of KYN, quinolinic acid, is an agonist for NMDA receptors; activation of NMDA receptors is associated with MDD. In contrast, ketamine is an antagonist of the NMDA receptor.

As described in the Examples herein, genomic variation in the AHR gene is associated with baseline plasma KYN levels in MDD patients. These studies also showed that SNPs in AHR are expression quantitative trait loci (eQTLs) for the AHR gene, and are associated with increased expression of IDO1 and TDO2—enzymes that catalyze the rate-limiting step for KYN biosynthesis (Karchner et al., supra). Thus, genetic variation in the AHR gene may be associated both with risk for MDD and response to ketamine therapy. Accordingly, this document is based at least in part on the development of data supporting the role of the AHR system in both the pathogenesis of MDD and the action of ketamine—a completely unanticipated series of observations.

Compounds

Compounds useful in the methods provided herein can act as agonists of the AHR system, and can lack the ability to bind to or interact with the glutamate receptor. Such compounds can fall into different categories of agonists/ligands for AHR. For example, compounds can be exogenous strong ligands/agonists, such as 3-methyl cholanthrene and dioxin, while others can be exogenous or endogenous weak ligands/agonists.

AHR ligands/agonists that may be useful in the methods provided herein include, without limitation, 3',4'-dimethoxy-α-naphthoflavone (DiMNF), a selective AHR modulator; 3,3'-diindolylmethane (DIM), another selective AHR modulator; kynurenine, an endogenous, and weak ligand; and nutritional compounds such as resveratrol and curcumin, which also are weak ligands for AHR. Further examples of activators of the AHR system are set forth in Nguyen and Bradfield (*Chem Res Toxicol* 21(1):102-116, 2008), which is incorporated herein by reference in its entirety. For example, endogenous and exogenous AHR ligands can include halogenated-dioxins and related compounds (e.g., halogenated-dibenzo-p-dioxins, -dibenzofurans, -azo(xy)benzenes, and -naphthalenes), polychlorinated biphenyls, polycyclic aromatic hydrocarbons, indigoids (e.g., indigo and indirubin), 2-(1'H-indole-3'-carbonyl)-thiazole-4-carboxylic acid methyl ester (ITE), equilenin (3-hydroxy-1,3,5(10),6,8-estrapentaen-17-one), arachidonic acid metabolites, heme metabolites, TRP metabolites, and dietary compounds such as indole-3-carbinol derivatives, and flavonoids. Non-ligand AHR agonists may include methylcellulose, cAMP, and low-density lipoprotein, for example. As noted above, weak agonists also may be useful, as may non-specific ligands. These include, without limitation, benzimidazoles.

The compounds provided herein, including pharmaceutically acceptable salts thereof, can be purchased commercially or prepared using organic synthesis techniques such as those that are known in the art. For example, a reaction for preparing a compound provided herein can be carried out in suitable solvents that can be readily selected by one of skill in the art of organic synthesis. Suitable solvents can be substantially non-reactive with the starting materials (reactants), the intermediates, or products at the temperatures at which the reactions are carried out, e.g., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of a compound can involve the protection and deprotection of various chemical groups. The need for protection and deprotection, and the selection of appropriate protecting groups, can be readily determined by one skilled in the art. The chemistry of protecting groups can be found, for example, in *Protecting Group Chemistry*, 1st Ed., Oxford University Press, 2000; and *March's Advanced Organic chemistry: Reactions, Mechanisms, and Structure*, 5th Ed., Wiley-Interscience Publication, 2001 (each of which is incorporated herein by reference in its entirety).

Compositions

This document also provides pharmaceutical compositions containing the AHR agonist compounds (or pharmaceutically acceptable salts thereof) as provided herein, in combination with a pharmaceutically acceptable carrier. The phrase "pharmaceutically acceptable" is used herein to refer to compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

Examples of pharmaceutically acceptable salts include acid addition salts and base salts.

Suitable acid addition salts are formed from acids that form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, hydrogen phosphate, isethionate, D- and L-lactate, malate, maleate, malonate, mesylate, methylsulphate, 2-napsylate, nicotinate, nitrate, orotate, oxalate, palmitate, pamoate, phosphate/hydrogen, phosphate/phosphate dihydrogen, pyroglutamate, saccharate, stearate, succinate, tannate, D- and L-tartrate, 1-hydroxy-2-naphthoate tosylate, and xinafoate salts.

Suitable base salts are formed from bases that form non-toxic salts. Examples include the aluminium, arginine, benzathine, calcium, choline, diethylamine, diolamine, glycine, lysine, magnesium, meglumine, olamine, potassium, sodium, tromethamine, and zinc salts.

Hemisalts (e.g., hemisulphate and hemicalcium salts) of acids and bases may also be formed.

A compound provided herein intended for pharmaceutical use can be administered as a crystalline or amorphous product. In some cases, such a product can be obtained, for example, as a solid plug, powder, or film by methods such as precipitation, crystallization, freeze drying, spray drying, or evaporative drying. Microwave or radio frequency drying may be used for this purpose.

A compound can be formulated for administration by any route, including orally, rectally, sublingually, and parenterally. Parenteral administration includes, for example, intravenous, intramuscular, intraarterial, intraperitoneal, intranasal, intravaginal, intravesical (e.g., to the bladder), intradermal, transdermal, topical or subcutaneous administration. Also contemplated is the installation of a compound in the body of a patient in a controlled formulation, with systemic or local release of a compound to occur at a later time. For example, a compound can be localized in a depot for controlled release to the circulation, or for release to a local site. Advantageously, a compound can be administered in the form of a pharmaceutical composition.

A pharmaceutical composition can containing one or more compounds as described herein, or an individual isomer, racemic or non-racemic mixture of isomers, or a pharmaceutically acceptable salt or solvate thereof, together with at least one pharmaceutically acceptable carrier, and optionally other therapeutic and/or prophylactic ingredients.

A pharmaceutical composition typically is administered as a formulation containing one or more compounds as provided herein in association with one or more pharmaceutically acceptable excipients or carriers. The term "excipient" or "carrier" is used herein to describe any ingredient other than a compound(s) provided herein. The choice of excipient will to a large extent depend on factors such as the particular mode of administration, the effect of the excipient on solubility and stability, and the nature of the dosage form.

Non-limiting examples of pharmaceutical carriers suitable for administration of the compounds provided herein include any such carriers known to those skilled in the art to be suitable for the particular mode of administration. Pharmaceutically acceptable carriers include, without limitation, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-b-cyclodextrins, or other solubilized derivatives can also be advantageously used to enhance delivery of a compound as provided herein. In some embodiments, the pharmaceutically acceptable carrier is a physiologically acceptable saline solution.

In some embodiments, pharmaceutical compositions can be formulated as solutions, suspensions, tablets, dispersible tablets, pills, capsules, powders, sustained release formulations or elixirs, for oral administration or in sterile solutions or suspensions for parenteral administration, as well as transdermal ointments, creams, gels, and patch preparations and dry powder inhalers (see, e.g., *Ansel Introduction to Pharmaceutical Dosage Forms, Fourth Edition* 1985, 126).

The concentration of a compound in a pharmaceutical composition will depend on absorption, inactivation, and excretion rates of the compound, the physicochemical characteristics of the compound, the dosage schedule, and the amount administered, as well as other factors known to those of skill in the art.

A pharmaceutical composition can be administered at once, or can be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The pharmaceutical compositions can be provided for administration to humans and animals in unit dosage forms, such as tablets, capsules, pills, powders, granules, sterile parenteral solutions or suspensions, oral solutions or suspensions, and oil-water emulsions containing suitable quantities of the compound(s). The pharmaceutically therapeutically active compounds are, in some embodiments, formulated and administered in unit-dosage forms or multiple-dosage forms. Unit-dose forms as used herein refers to physically discrete units suitable for human and animal patients and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses that are not segregated in packaging.

Liquid pharmaceutically administrable compositions can be prepared by, for example, dissolving, dispersing, or otherwise mixing a compound as provided herein and optional pharmaceutical adjuvants in a carrier such as, without limitation, water, saline, aqueous dextrose, glycerol, glycols, ethanol, and the like, to form a solution or suspension. If desired, a pharmaceutical composition to be administered also can contain minor amounts of nontoxic auxiliary substances such as wetting agents, emulsifying agents, solubilizing agents, pH buffering agents and the like (e.g., acetate, sodium citrate, cyclodextrine derivatives, sorbitan monolaurate, triethanolamine sodium acetate, triethanolamine oleate, and other such agents).

Dosage forms or compositions can contain a compound as provided herein in the range of 0.005% to 100%, with the balance made up from one or more non-toxic carriers. Methods for preparation of these compositions are known to those skilled in the art. The contemplated compositions may contain 0.001%-100% active ingredient. In some embodiments, for example, a composition can contain 0.1-95% active ingredient, and in other embodiments, a composition can contain 75-85% active ingredient.

Pharmaceutical compositions suitable for the delivery of compounds provided herein, as well as methods for their preparation, will be readily apparent to those skilled in the art. Such compositions and methods for their preparation can be found, for example, in Remington's Pharmaceutical Sciences, 19th Edition (Mack Publishing Company, 1995).

Methods of Screening

Also provided herein are methods of screening for compounds that may be useful for treating depressive disorders by activating the AHR system. Such compounds can be identified as being are agonists of the AHR system, while not interacting with (e.g., binding to) a glutamate receptor. The methods can include, for example, performing an assay to determine whether a candidate compound (e.g., a compounded tested individually or a compound contained within a population of compounds that are tested together) can activate the AHR system, and also performing an assay to determine whether the candidate compound binds to or otherwise interacts with the glutamate receptor (e.g., the NMDA receptor).

Any suitable method can be used to test the ability of a candidate compound or plurality of candidate compounds to agonistically affect the AHR system. In some embodiments, for example, the expression level of AHR, AHRR, or ARNT in a cell treated with a candidate compound can be assessed to determine whether the AHR system has been activated. If the level of AHR and/or ARNT mRNA or protein are increased in the cell, or if the level of AHRR mRNA or protein is decreased in the cell, then the compound can be identified as an AHR agonist.

Further, any suitable method can be used to test the ability of a candidate compound or plurality of candidate compounds to interact with a glutamate receptor. In some embodiments, for example, co-immunoprecipitation (e.g., of lysates from cells treated with the candidate(s)) can be used, or the level of kynurenine secreted from treated cells can be measured. An increase in the level of secreted kynurenine from treated cells, relative to the level secreted from untreated cells, can indicate that the candidate(s) interact with the glutamate receptor.

Methods of Treatment

This document also provides methods for treating a depressive disorder in a subject. The methods can include, for example administering to a subject (e.g., a human or an animal) in need thereof (e.g., an individual diagnosed as having MDD), a compound or pharmaceutical composition as described herein.

The terms "treating" and "treatment" mean causing a therapeutically beneficial effect, such as ameliorating one or more existing symptoms and/or reducing the severity of symptoms that will or are expected to develop.

A "therapeutically effective" amount of a compound or composition as described herein is typically one that is sufficient to achieve the desired effect and may vary according to the nature and severity of the disease condition, and the potency of the compound. It will be appreciated that different concentrations may be employed for prophylaxis than for treatment of an active disease.

The term "contacting" means bringing at least two moieties together, whether in an in vitro system or an in vivo system.

As used herein, "administration" refers to delivery of a compound or composition containing a compound provided herein by any external route, including, without limitation, intravenous, intramuscular, subcutaneous, intranasal, inhalation, transdermal, oral, buccal, rectal, sublingual, and parenteral administration.

In the methods provided herein, any appropriate method can be used to administer a compound or composition to a subject. Administration can be, for example, parenteral (e.g., by subcutaneous, intrathecal, intraventricular, intramuscular, or intraperitoneal injection, or by intravenous drip). Administration can be rapid (e.g., by injection) or can occur over a period of time (e.g., by slow infusion or administration of slow release formulations). In some embodiments, administration can be topical (e.g., transdermal, sublingual, ophthalmic, or intranasal), pulmonary (e.g., by inhalation or insufflation of powders or aerosols), or oral.

A compound provided herein can be administered to a subject in an appropriate amount, at an appropriate frequency, and for an appropriate duration effective to achieve a desired outcome (e.g., to reduce one or more clinical symptoms or molecular/cellular hallmarks of a depressive disorder such as MDD). When the disease is MDD, symptoms and hallmarks that can be alleviated by treatment with a compound or composition as provided herein include, for example, low mood, inability to experience pleasure in activities that were formerly enjoyed, thoughts and feelings of worthlessness, inappropriate guilt or regret, helplessness, hopelessness, self-hatred, delusions, hallucinations, poor concentration and memory, withdrawal from social situations and activities, reduced sex drive, thoughts of death or suicide, insomnia, hypersomnia, fatigue, headaches, digestive problems, decreased or increased appetite, agitation, lethargy, forgetfulness, and slowing of movement. Thus, administration of an effective amount of a compound or composition as provided herein can result an improvement in any of these symptoms/hallmarks. Any suitable method can be used to assess such symptoms, including standard clinical tests for evaluating depression.

Optimum dosages of a compound or composition as provided herein can vary depending on the relative potency of individual compounds, and can generally be estimated based on $EC_{50}$ found to be effective in in vitro and in vivo animal models. Dosages may fall within the range from 0.5 mg to 500 mg. For example, an effective amount of a compound as provided herein can be from about 0.5 mg to about 1 mg, about 1 mg to about 5 mg, about 5 mg to about 10 mg, about 10 mg to about 25 mg, about 25 mg to about 50 mg, about 50 to about 100 mg, about 100 mg to about 250 mg, or about 250 mg to about 500 mg. If a particular subject fails to respond to a particular amount, then the amount of the compound or composition can be increased by, for example, two fold. After receiving this higher concentration, the subject can be monitored for both responsiveness to the treatment and toxicity symptoms, and adjustments made accordingly. The effective amount can remain constant or can be adjusted as a sliding scale or variable dose depending on the subject's response to treatment. Various factors can influence the actual effective amount used for a particular application. For example, the frequency of administration, duration of treatment, and severity of disease may require an increase or decrease in the actual effective amount administered.

The frequency of administration can be any frequency that has a desired effect (e.g., reducing one or more clinical symptoms or molecular/cellular hallmarks of a depressive disorder), without producing significant toxicity. For example, the frequency of administration can be once or more daily, biweekly, weekly, monthly, or even less. The frequency of administration can remain constant or can be variable during the duration of treatment. A course of treatment can include rest periods. For example, a composition containing one or more compounds as provided herein can be administered over a two week period followed by a two week rest period, and such a regimen can be repeated multiple times. As with the effective amount, various factors can influence the actual frequency of administration used for a particular application. For example, the effective amount, duration of treatment, route of administration, and severity of disease may require an increase or decrease in administration frequency.

An effective duration for administering a compound provided herein can be any duration that has a desired effect (e.g., reducing one or more clinical symptoms or molecular/cellular hallmarks of a depressive disorder), without producing significant toxicity. Thus, an effective duration can vary from several days to several weeks, months, or years, but in general, an effective duration for treatment of depression can extend for number of years, such that an effective duration can be for as long as an individual subject is alive. Multiple factors can influence the actual effective duration used for a particular treatment. For example, an effective duration can vary with the frequency of administration, effective amount, use of multiple treatment agents, route of administration, and severity of the disease.

After administering a compound or composition as provided herein to subject having a depressive disorder such as MDD, the subject can be monitored to determine whether or not their condition as improved. For MDD, for example, a subject can be assessed after treatment to determine whether or not a symptom of MDD has been reduced. Methods for assessing symptoms and hallmarks of MDD include those known in the art, for example.

Also provided herein are articles of manufacture containing one or more compounds as described herein, or a pharmaceutical composition containing one or more compounds as described herein, in combination with a pharmaceutically acceptable carrier, for example. The compound or composition can be within a container (e.g., a bottle, vial, or syringe). The article of manufacture also can include a label with directions for reconstituting and/or using the compound(s) or composition. In some embodiments, an article of manufacture can include one or more additional items (e.g., one or more buffers, diluents, filters, needles, syringes, and/or package inserts with further instructions for use).

The invention will be further described in the following examples, which do not limit the scope of the invention described in the claims.

EXAMPLES

Example 1—Materials and Methods

Study Population:

906 patients were enrolled in an antidepressant clinical trial conducted by the Mayo Clinic, Rochester, Minn. All patients were diagnosed with MDD by clinicians with the HAM-D (Hamilton Depression Rating) score more than 14. The patients did not have other psychiatric comorbidities such as psychosis or mania. The patients were treated with SSRI (either citalopram 20 mg or escitalopram 10 mg) for 8 weeks. Symptomatic evaluation of the patients were carried out both at 4-week and at 8-week of therapy to assess response and/or remission to the therapies. Response and remission were defined as 50% or more reduction and score less than 5 in the Quick Inventory of Depression Symptomatology (QIDS), respectively. Blood samples were drawn at the baseline, at 4-week of therapy and at 8-week of therapy. A portion of blood sample, drawn at baseline from all 906 patients was used to extract DNA for the GWAS study. To extract plasma from the EDTA containing blood, the samples were centrifuged at 8000×g for 20 minutes. The collected plasma samples were further centrifuged to ensure complete removal of platelets. The isolated plasma samples were stored at −80° C. and later on shipped on dry ice for metabolomic profiling.

Metabolomic Assays:

Plasma samples from a total of 306 patients collected at three time points (baseline, 4-week and 8-week) were utilized to quantify selective metabolites. A quantitative Liquid Chromatography and Electrochemical Array (LC-ECA) was utilized to measure 37 metabolites, which were products of tryptophan, several monoamine and purine pathways. Detail of metabolomics profiling has been discussed elsewhere (Ji et al., *Clin Pharmacol Ther* 89(1):97-104, 2011).

SNP Genotyping:

For genome-wide SNP analysis, DNA from LCLs was genotyped using Illumina HumanHap 550K and 510S BeadChips. Genotyping was performed in the Genotype Shared Resource (GSR) at the Mayo Clinic, Rochester, Minn.

Cell Culture:

Human glioblastoma cells were purchased from American Type Culture Collection (ATCC, Manassas, Va.) and grown in 75 cm$^2$ flasks with DMEM media supplemented with 10% fetal bovine serum. Two different glioblastoma cell lines (U251 and U87) were used in the study. Once the flasks were 80% confluent, the culture media was aspirated, and cells were washed with sterile PBS and then detached from the flasks by adding trypsin-EDTA. Trypsin-EDTA was neutralized by complete serum containing media, and cells were counted using an automated cell counter (Bio-Rad, Hercules, Calif.). Either 150,000 or 300,000 cells were plated onto each well of a 24 or 12-well cell culture plate, and were used for knockdown or over expression experiments.

Human induced pluripotent stem cells (iPSCs) were purchased from Axol, UK and were differentiated as per the company's protocol. The cells were differentiated for 30 days before being used for lentivirus-mediated knockdown experiments.

MDD patients' derived iPSCs were generated from biopsied fibroblasts obtained from five SSRI remitters, five non-remitters, and also from five age and sex-matched controls.

Lymphoblastoid cell lines (LCL) containing a human variation panel were grown as described elsewhere (Niu et al., *Genome Res* 20(11):1482-1492, 2010). Six LCLs with homozygous wild type (wt/wt) and six LCLs with homozygous variant (v/v) genotypes for the AHR SNP (r57791070) were cultured for 15 days. Cells were collected in individual microfuge tubes and centrifuged at 200×g for 15 minutes. The supernatant media samples were discarded and 1 mL of PBS was added onto the tubes, followed by centrifugation for 10 minutes. The PBS was aspirated out and the cells were lysed by adding M-PER buffer, supplemented with a protease inhibitor cocktail (Thermo).

Transient Transfection:

Glioblastoma cells (both U251 and U87) were transfected separately by AHR and ARNT siRNAs (Smartpool, GE Healthcare, Lafayette, Colo.) using LIPOFECTAMINE® RNAiMAX (Life Technologies, Grand Island, N.Y.). Briefly, the siRNAs and RNAiMAX were dissolved separately in low serum media (Opti-MEM®) and incubated for five minutes to allow RNA-lipid complex to form. The complex was added directly to the wells. siRNA targeting non-eukaryotic mRNAs was also used and served as a negative control. Similarly, AHR cDNA (OriGene Technologies, Inc., Rockville, Md.), ARNT cDNA (GeneCopoeia, Inc., Rockville, Md.), and AHRRΔ8 cDNA (provided by Dr. Mark Hahn) also were separately transfected into the glioblastoma cells following a similar transfection protocol using LIPOFECTAMINE® 2000 (Life Technologies) as transfection reagent. For both siRNA and cDNA transfection, the media was replaced by fresh growth media after 8-12 hours and the cells were harvested either after 24 or 40 hours. During the harvest, the conditioned media samples were collected, centrifuged 10 minutes at 200×g and the supernatant media was stored at −80° C. and later on used to detect secreted kynurenine levels. The cells on the wells were washed once with ice-cold PBS, and lysed directly on the plate using M-PER® buffer (Thermo Scientific, Rockford, Ill.) and stored for protein detection by Western immunoblotting. Cells from some of the wells were lysed by RNA lysis buffer (Zymo Research, Irvine, Calif.) and either stored at −80° C. or used for preparation of RNA for RT-qPCR analyses.

Quantification of mRNA Expression Following Knocking Down or Overexpression of AHR, ARNT and AHRR:

Lysates obtained from cells subjected to knockdown or overexpression were used to isolate total RNA (Zymo Research). The purity of the extracted RNA samples was assessed using a Nanodrop instrument (Thermo Scientific). All samples had acceptable $A_{260}/A_{280}$ ratios. AHR, ARNT, AHRR, IDO1, and TDO2 mRNAs levels were quantified by reverse transcription quantitative PCR (RT-qPCR) using a one step RNA-to-Ct™ kit (Life Technologies). The kit contains reagents for converting RNA to cDNA, followed by primer-specific amplification of the desired mRNA (in this case, AHR, ARNT, AHRR, IDO1, and TDO2). GAPDH was used as a reference gene. The quantification of these mRNAs was carried out by employing the ΔΔCt method as described elsewhere (Ingle et al., *Cancer Discovery* 3(7):812-825, 2013).

Western Immunoblotting:

Cell lysates obtained after transfections and from LCLs were subjected to Western immunoblotting to detect levels of AHR, AHRR, ARNT, TDO2, and IDO1 proteins. Briefly, equal amounts of protein (as determined by the BCA protein assay) were loaded onto premade Criterion gels (Bio-Rad) and run for 1 hour at 180V. Proteins from the gels were electrophoretically transferred onto PVDF membranes and blocked at room temperature for 1 hour with 5% non-fat milk dissolved in TBST. The membranes were incubated with primary antibodies (anti-AHR from GeneTex, Inc. (Irvine, Calif.); anti-ARNT and anti AHRR from Sigma (St. Louis, Mo.); TDO2 from OriGene Technologies, Inc.; and IDO1) dissolved in 5% non-fat milk containing TBST at 4° C. overnight with gentle rocking. Following incubation, the membranes were vigorously washed with TB ST several times and then incubated with appropriate secondary antibodies, dissolved in 5% non-fat milk containing TBST at room temperature for 1 hour. Several TBST washes were carried out before ECL reagents were applied to the membranes and radiographic images were captured on X-ray films (GE). B-actin protein also was detected and served as a loading control. Quantification of Western immunoblots was carried out using NIH Image-J (Abramoff et al., *Biophotonics Intl* 11(7):36-42, 2004), and plotted in GraphPad-Prism software.

Chromatin Immunoprecipitation (ChIP) Assays:

Binding of AHRR to the XREs present in AHR, AHRR, IDO1, and TDO2 genes were evaluated by ChIP using a commercially available kit (EpiTect, Qiagen, Germantown, Md.) following the manufacturer's instructions. Briefly, transfected U251 cells were fixed in 4% paraformaldehyde and sonicated several times to obtain chromatin. Before proceeding to the next step, formation of chromatin was assessed by running the lysates in a 2% agarose gel. Formed chromatin was incubated with AHRR antibody (from Dr. Mark Hahn) overnight at 4° C. on a rotator. AHRR antibody-bound chromatin was used to assess binding of AHRR to the XREs by PCR with appropriate primers. The final PCR products were run on 2% agarose gels, and the images were captured in a gel-documentation system (Bio-Rad Laboratories, Hercules, Calif.).

Kynurenine Measurement:

Levels of secreted kynurenine were measured using HPLC.

AHRR Promoter Activity Assays:

An AHRR promoter containing functional and mutated XREs as described elsewhere (Haarmann-Stemmann et al., *Drug Metab Dispos* 35(12):2262-2269, 2007) was obtained from Dr. Thomas Haarmann-Stemmann. Promoter constructs were tagged with a luciferase activity-containing fragment. U251 glioblastoma cells were co-transfected with intact XRE or mutated XRE-containing promoter constructs and either AHR or ARNT siRNA for 24 hours. Lysates were subjected to luciferase detection assay using a DUAL-GLO® Luciferase assay kit (Promega, Madison, Wis.). Luminometric signals were recorded using a luminometer (Bio-Rad Laboratories). An empty backbone vector (pGL3-basic) was used to evaluate any non-specific activity.

Statistical Analyses:

Statistical analyses between the groups were carried out using GraphPad Prism software by T-test, where the α-value was set at 0.05.

Example 2—Pharmacometabolomics-Informed Pharmacogenomics Signals in AHR

Figure 3:
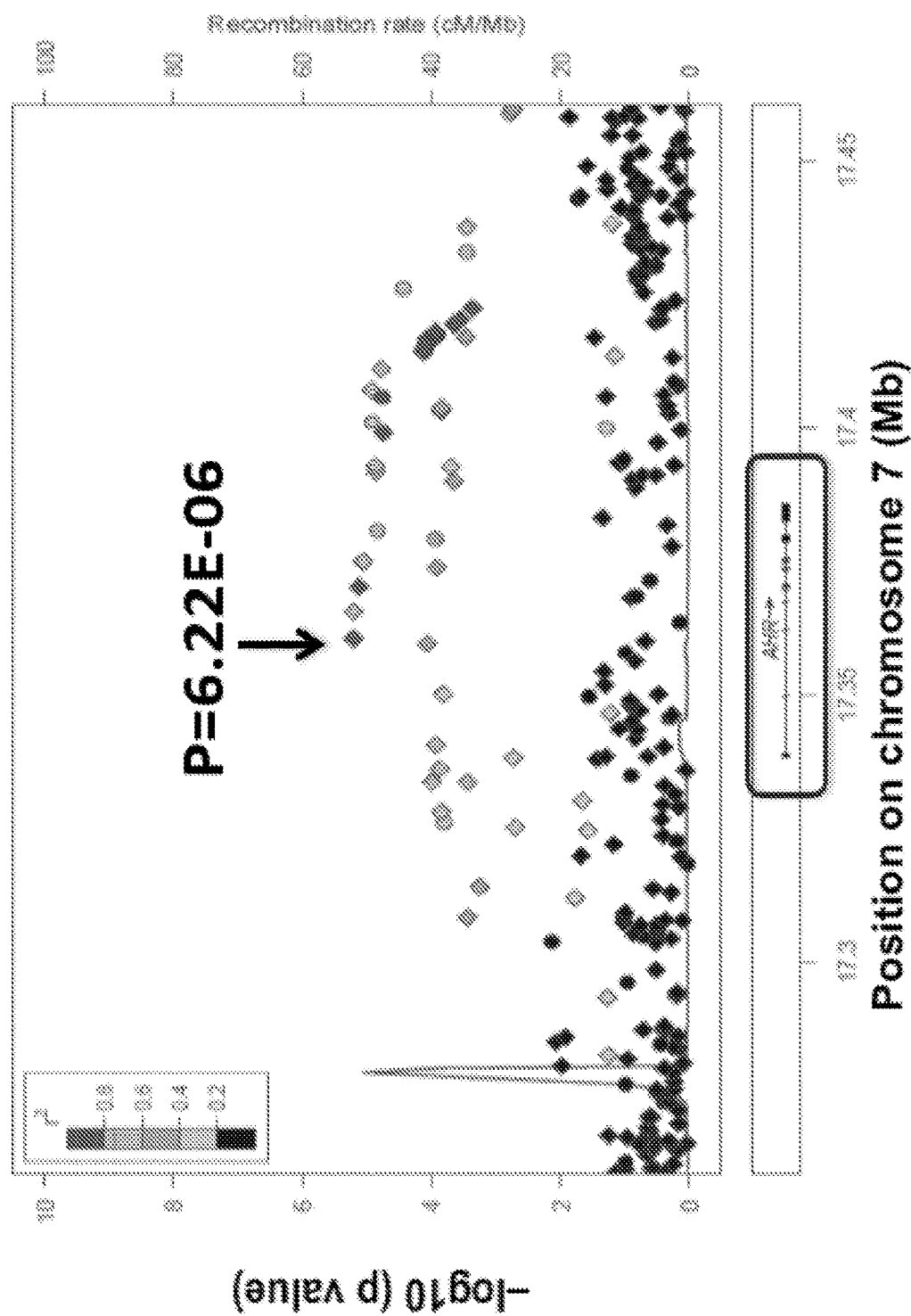
FIG. 3 is a graph plotting the genetic association of plasma kynurenine levels with loci on chromosome 7, showing that single nucleotide polymorphisms (SNPs) associated with AHR signals were in tight linkage disequilibrium (LD).

Genetic association of plasma KYN levels at baseline and after 4 weeks and 8 weeks of treatment revealed SNP signals in and around AHR. SNPs associated with AHR signals (top SNP p value $6.22 \times 10^{-6}$; FIG. 3) were in tight linkage disequilibrium (LD). The same SNP signals were shown to be associated with the 4-week and 8-week plasma KYN levels, albeit less significantly.

Example 3—AHR SNPs are eQTL for AHR Gene Expression

Figure 4:
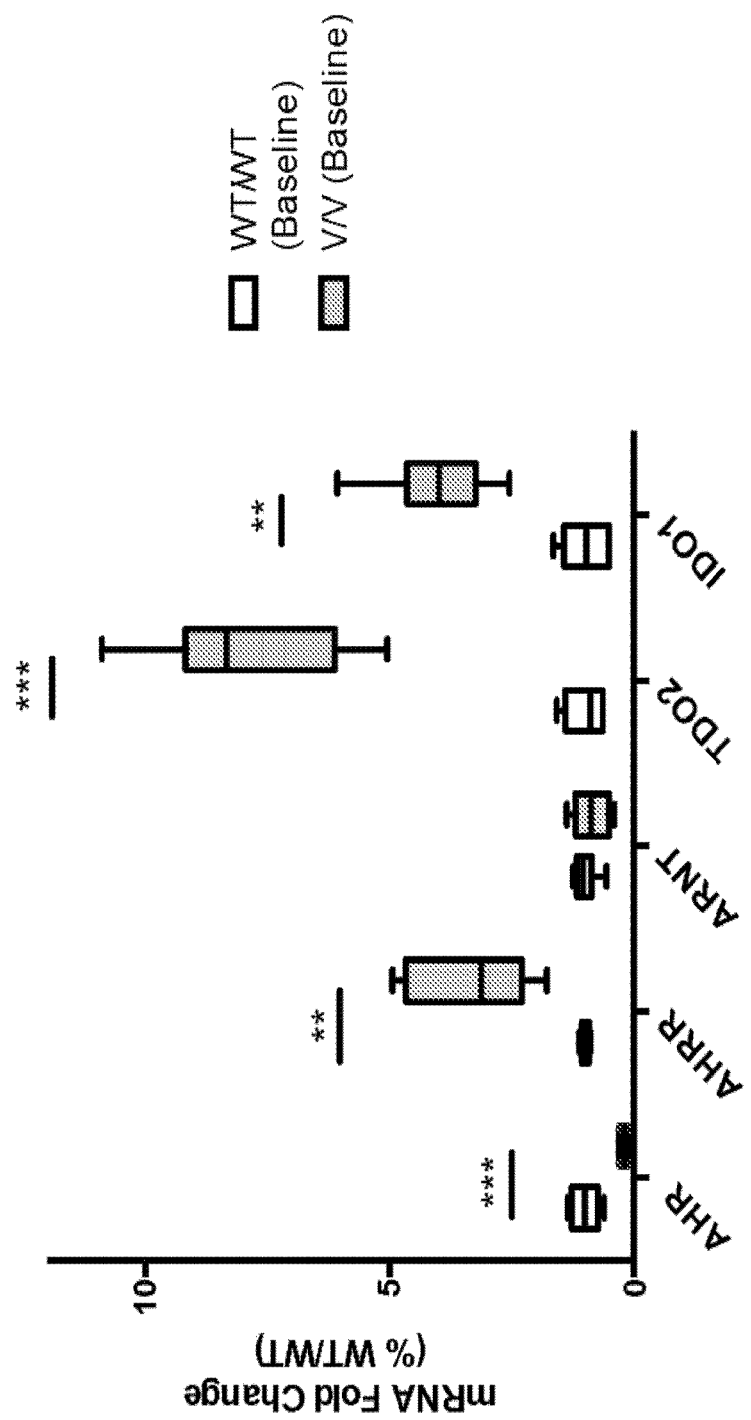
FIG. 4 is a graph plotting relative mRNA levels for AHR, AHRR, ARNT, tryptophan 2,3 dioxygenase (TDO2), and indolamine 2,3 dioxygenase 1 (IDO1) in lymphoblastoid cell lines (LCL) that are homozygous wild type for the rs7791070 AHR SNP, or homozygous variant for rs7791070. n=6; p<0.01; *p<0.001.
Figure 5A:
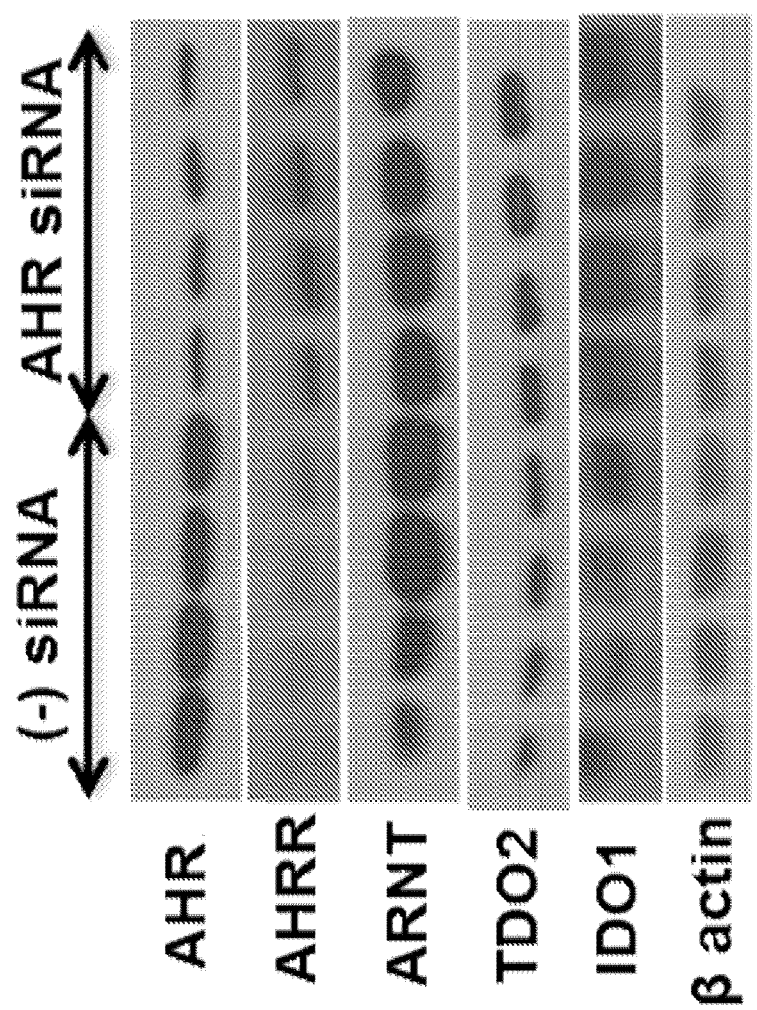
FIG. 5A is a picture of a Western blot showing levels of AHR, AHRR, ARNT, TDO2, IDO1, and β-actin in glioblastoma cells after treatment of the cells with control or AHR small interfering RNA (siRNA).
Figure 5C:
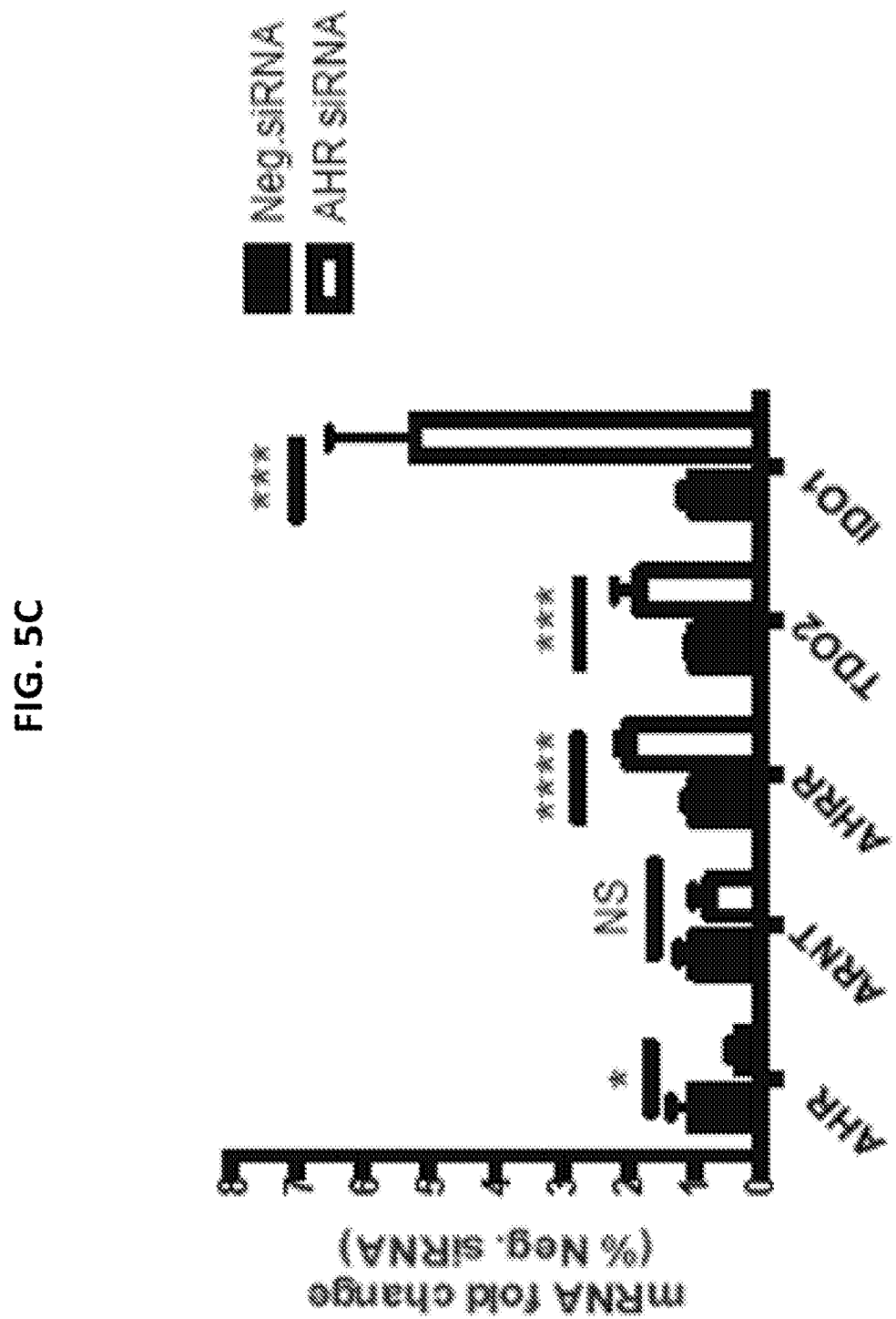
FIG. 5C is a graph plotting mRNA levels for AHR, ARNT, AHRR, TDO2, and IDO1 in U251 glioma cells after treatment of the cells with control or AHR siRNA. n=4; *p<0.001; **p<0.0001; NS, not significant.

The SNPs associated with plasma KYN levels were evaluated for eQTLs (i.e., whether the SNPs were associated with AHR expression, both in the brain and in the periphery). Analysis of the "Brain-Cloud" dataset and revealed that AHR SNPs are associated with lower expression of AHR. AHR expression also was evaluated in LCL containing a human genomic variation panel, as described elsewhere (Ellsworth et al., *Pharmacogenet Genom* 23(3):156-166, 2013). Protein analysis by Western immunoblotting revealed decreased expression of AHR in the LCL samples homozygous for the AHR variant (v/v), as compared to LCLs with AHR homozygous wild type (WT/WT) SNPs (FIG. 4).

Example 4—AHR, AHRR, and ARNT Knockdown in Glioblastoma Cells

Knocking down AHR and ARNT in both clones of glioblastoma cells (U251 and U87) revealed increased mRNA and protein expression of one of the rate-limiting enzymes for KYN synthesis—in particular, TDO2 (FIGS. 5A, 5B, 5C, 6A, 6B, and 6C). Expression of another KYN biosynthetic enzyme, IDO1, also was increased in U251 glioblastoma cells (FIGS. 5A, 5B, 5C, 6A, 6B, and 6C). Concomitantly, increased expression of AHRR also was observed in both AHR and ARNT knockdown cells (FIGS. 5A, 5B, 5C, 6A, 6B, and 6C).

Figure 7A:
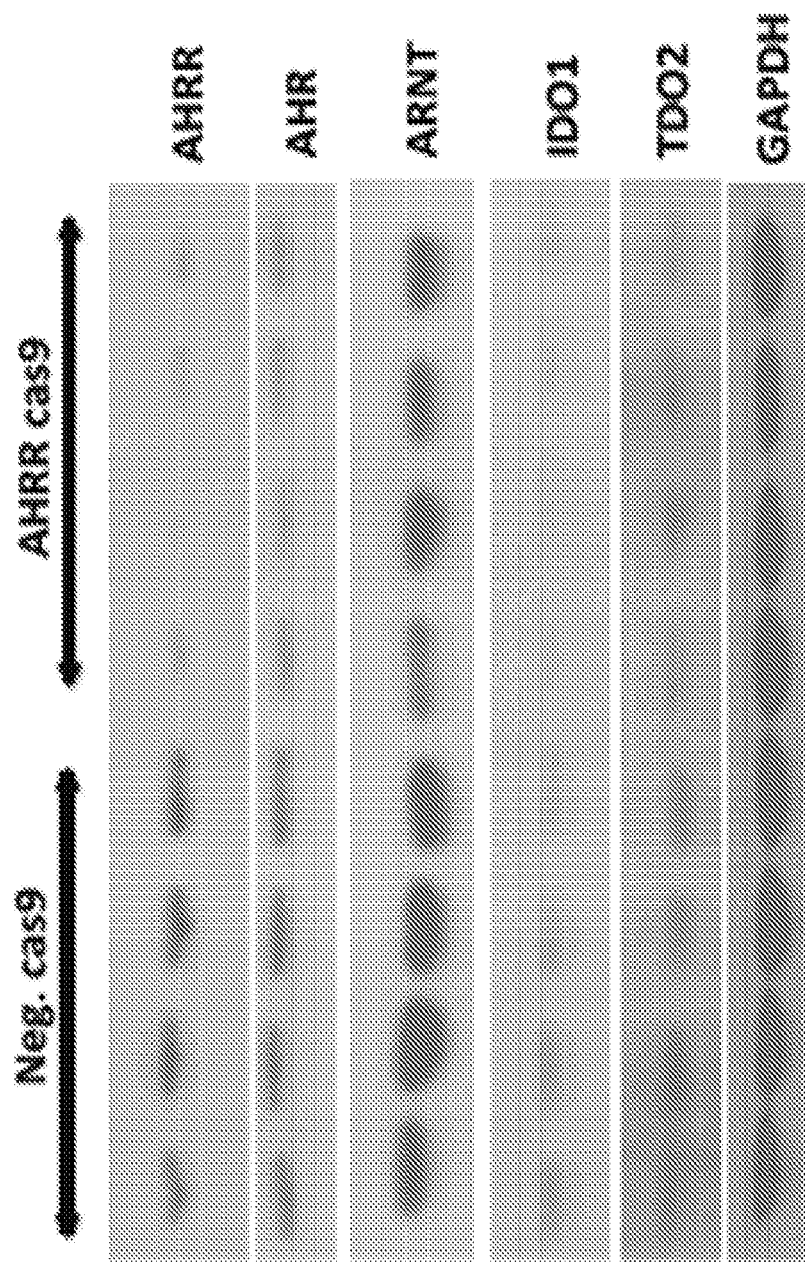
FIG. 7A is a picture of a Western blot showing levels of AHRR, AHR, ARNT, TDO2, IDO1, and GAPDH in U251 glioblastoma cells after treatment of the cells with control or cas9 AHRR for CRISPR-mediated AHRR knockout.
Figure 7B:
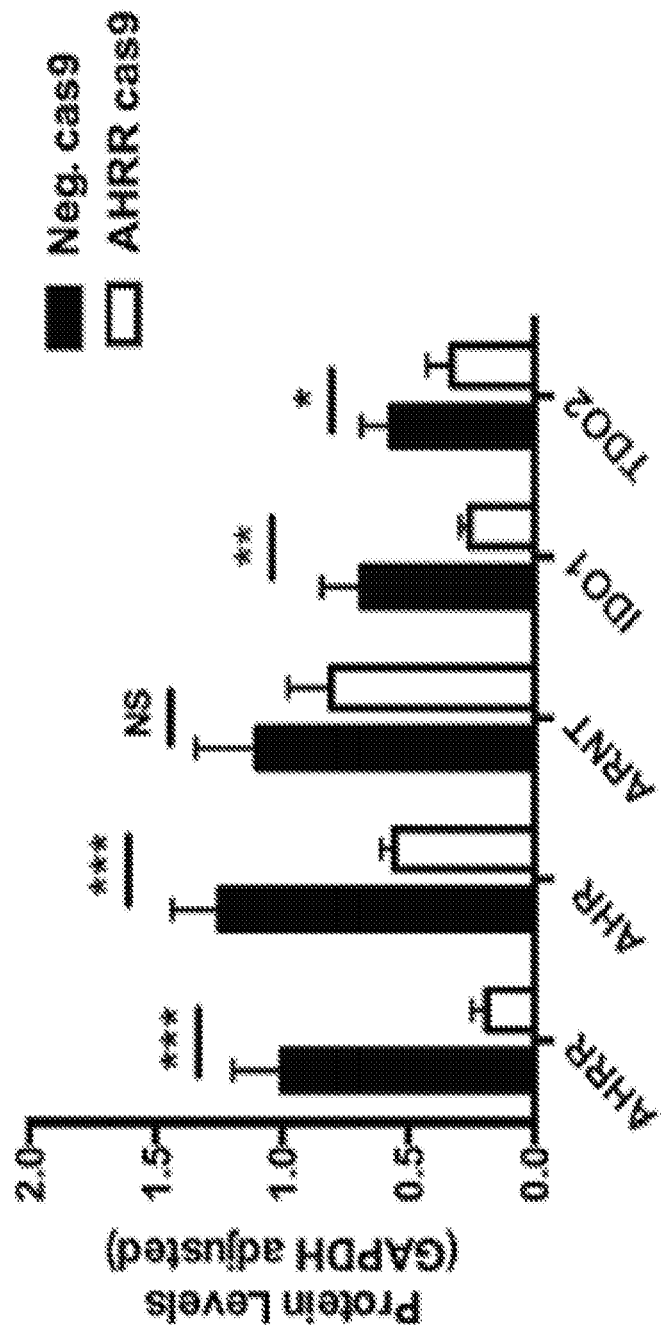
FIG. 7B is a graph plotting GAPDH-adjusted protein levels for AHRR, AHR, ARNT, TDO2, and IDOL as determined from the Western blot shown in FIG. 7A. n=4; p<0.01; *p<0.001, NS, not significant.

In contrast, glioblastoma cells transfected with CRISPR/Cas targeted to AHRR exhibited decreased expression of IDO1 (for U251 cells) and TDO2 (both U251 and U87 cells), and expression of AHR and ARNT also was decreased (FIGS. 7A and 7B).

Figure 6B:
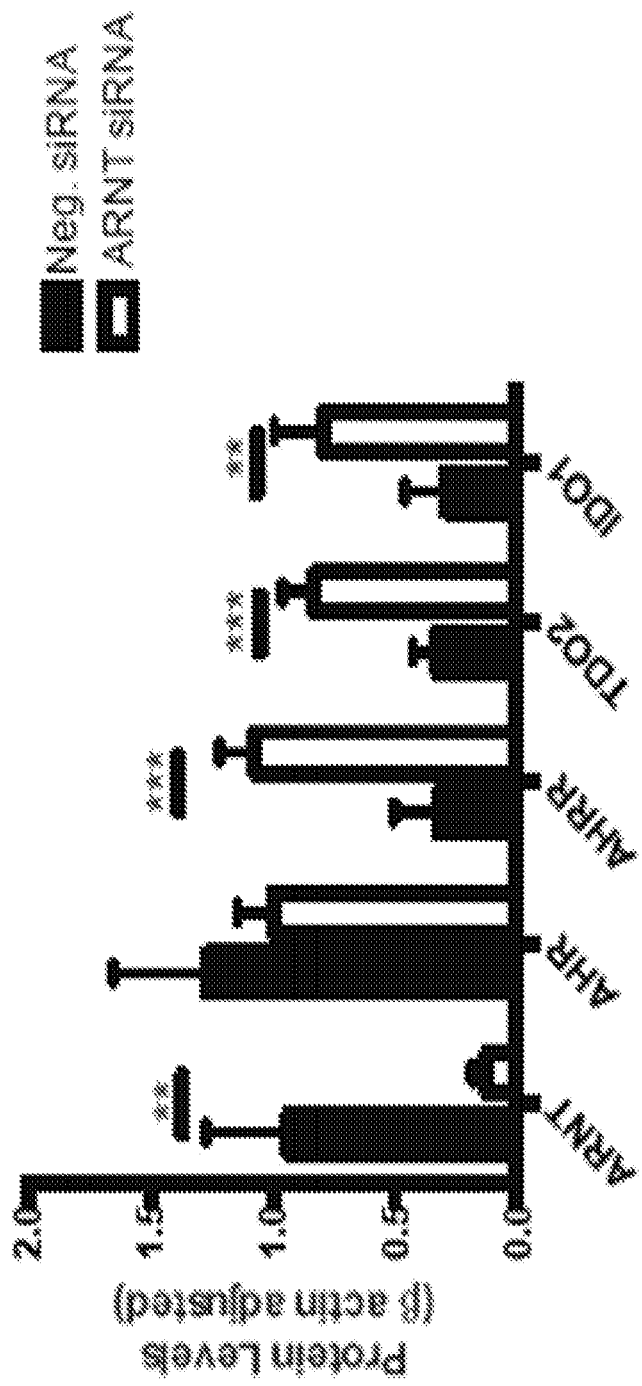
FIG. 6B is a graph plotting β-actin-adjusted protein levels for ARNT, AHR, AHRR, TDO2, and IDO1, as determined from the Western blot shown in FIG. 6A. n=4; p<0.01; *p<0.001.
Figure 6D:
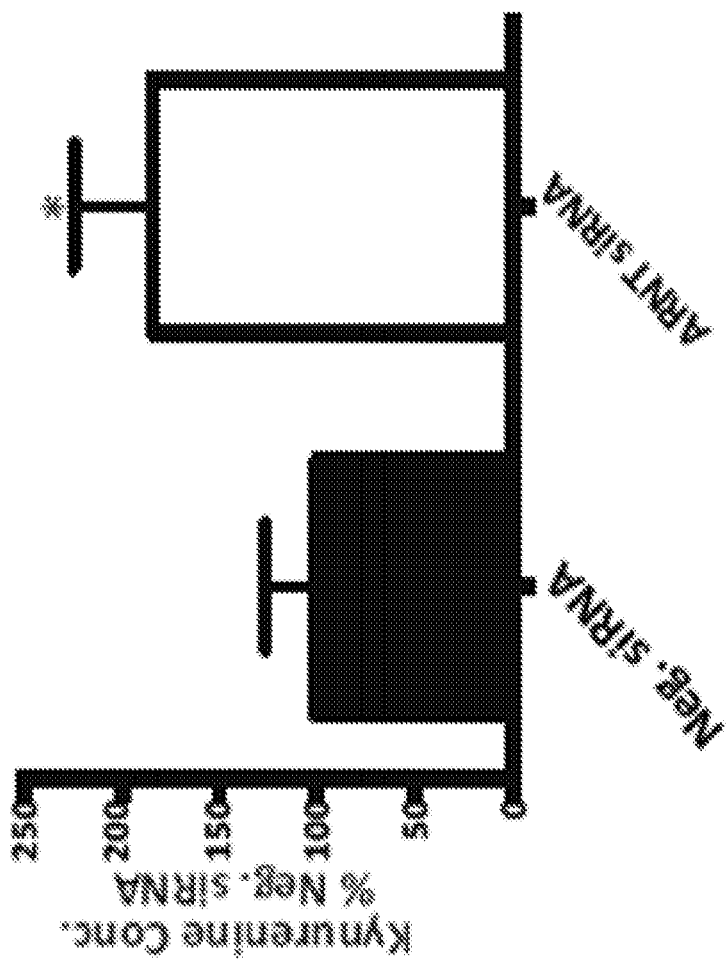
FIG. 6D is a graph plotting the concentration of kynurenine secreted by U251 glioma cells treated with control or ARNT siRNA. n=4; *p<0.05.

KYN concentrations, as determined by HPLC, were decreased in conditioned media samples of both AHR and ARNT knocked down U251 (FIGS. 5D and 6D) and U87 cells. The KYN concentration also was estimated to be decreased in conditioned media samples of both U251 and U87 cells after knocking down AHRR (FIG. 7C).

Example 5—AHRR Over-Expression in the Glioblastoma Cells

Figure 7D:
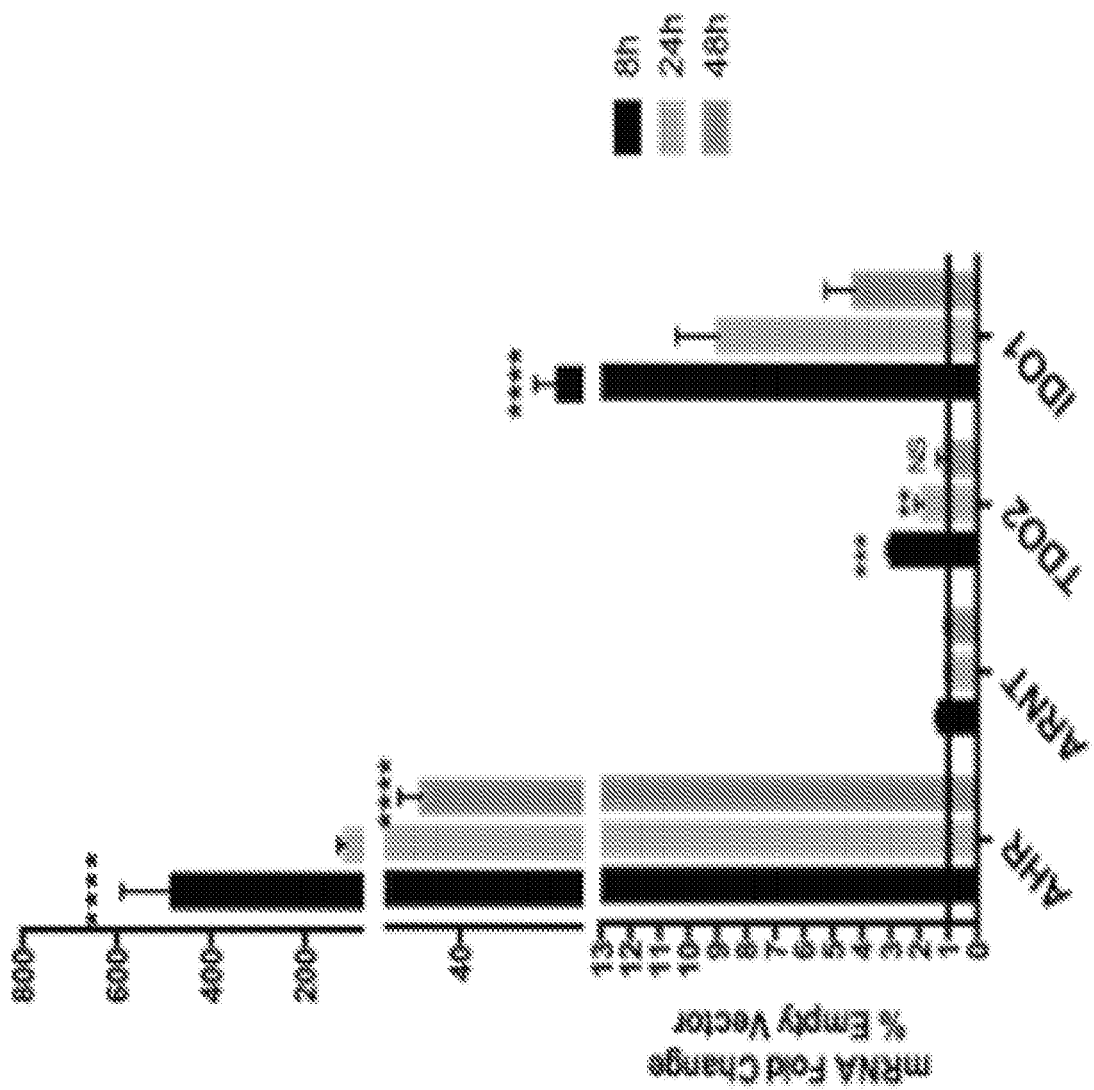
FIG. 7D is a graph plotting a time course of mRNA levels for AHR, ARNT, TDO2, and IDO1 with the indicated length of AHRR overexpression. n=4; p<0.01; *p<0.001; ****p<0.0001; ns, not significant.
Figure 8A:
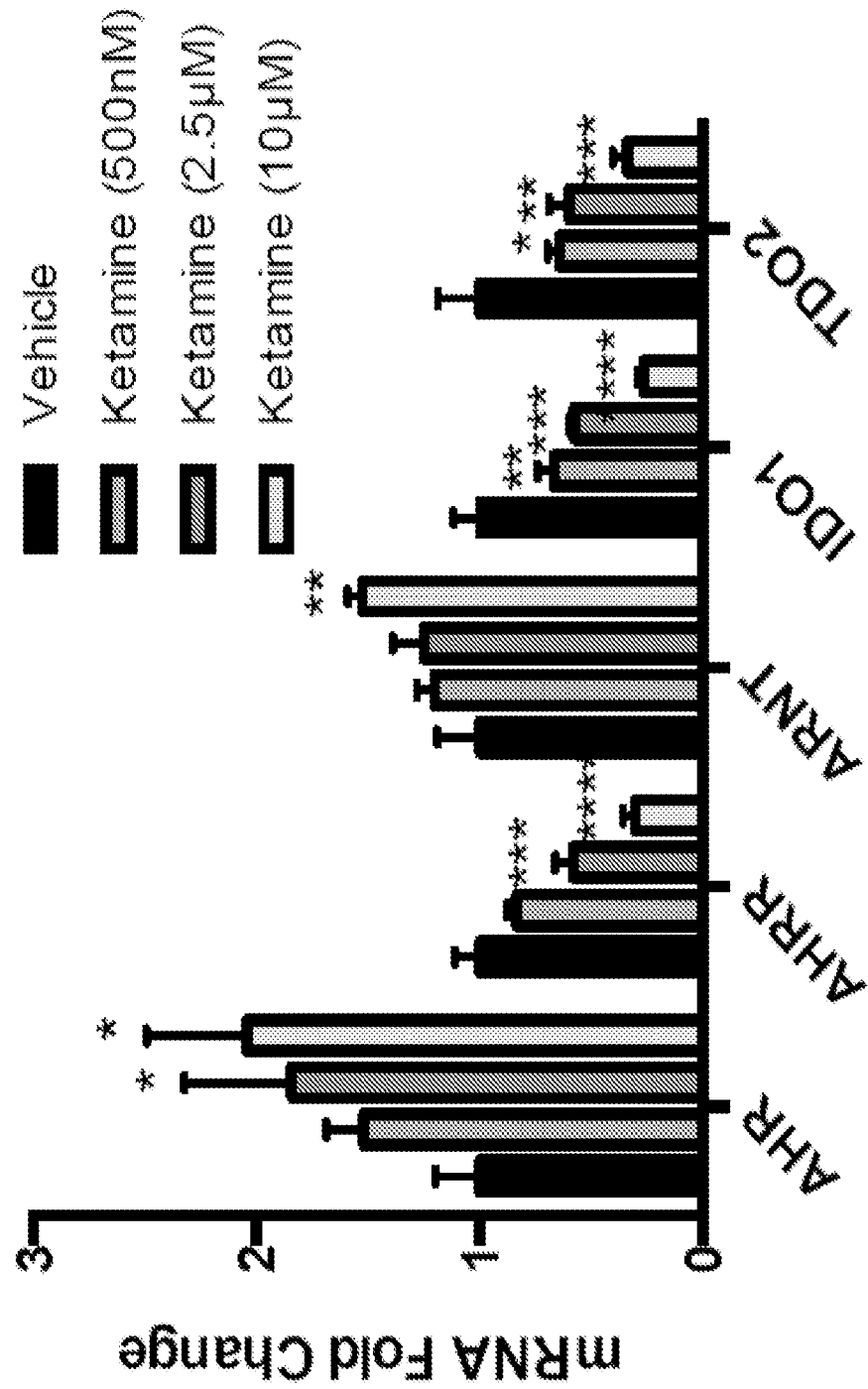
FIG. 8A is a graph plotting the change in mRNA levels for AHR, AHRR, ARNT, IDOL and TDO2 after treatment of U251 glioma cells with vehicle or the indicated concentrations of ketamine.
Figure 8B:
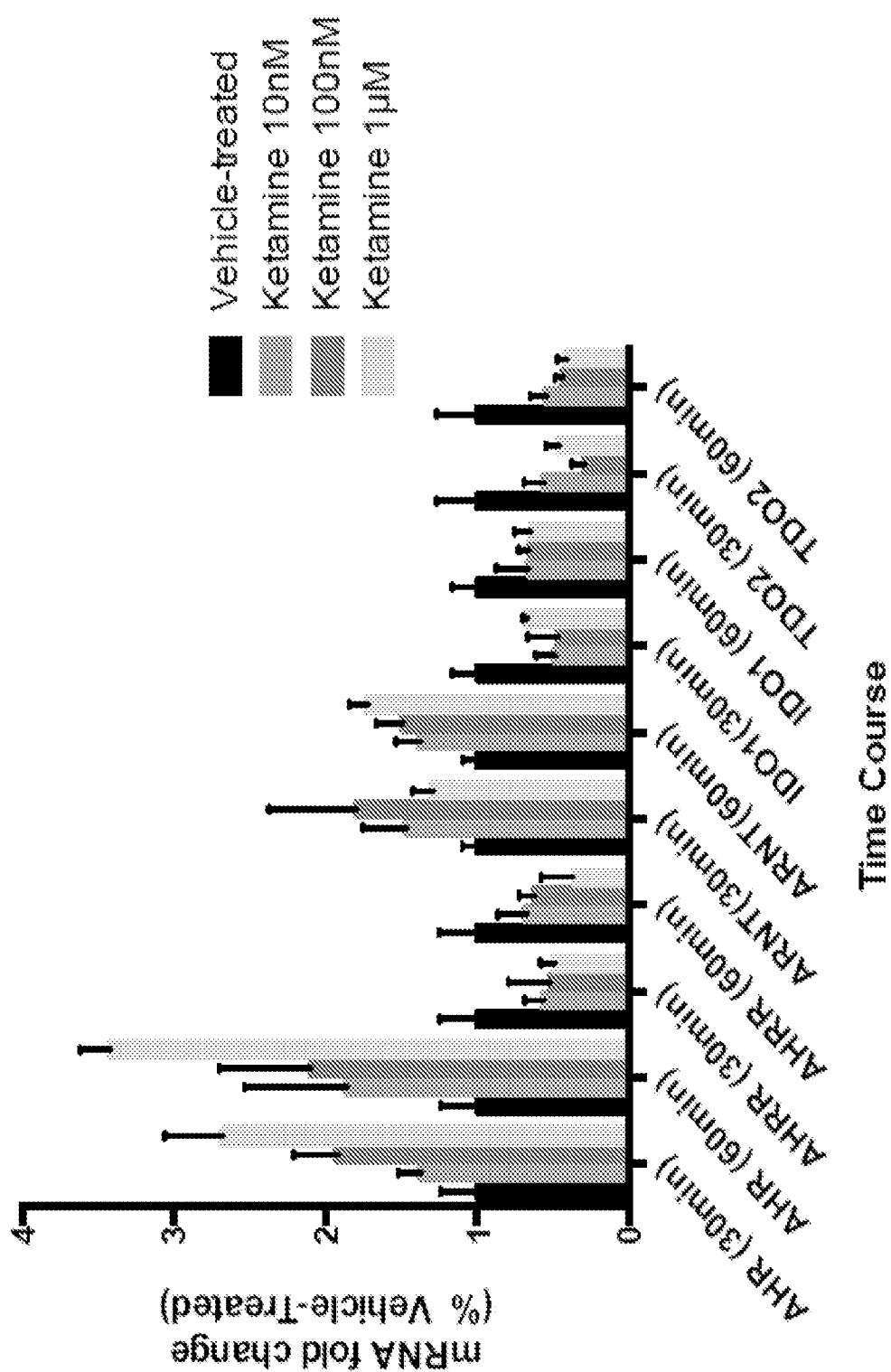
FIG. 8B is a graph plotting the change in mRNA levels for AHR, AHRR, ARNT, IDOL and TDO2 after treatment of U251 glioma cells with vehicle or the indicated concentrations of ketamine, for the indicated lengths of time.
Figure 8C:
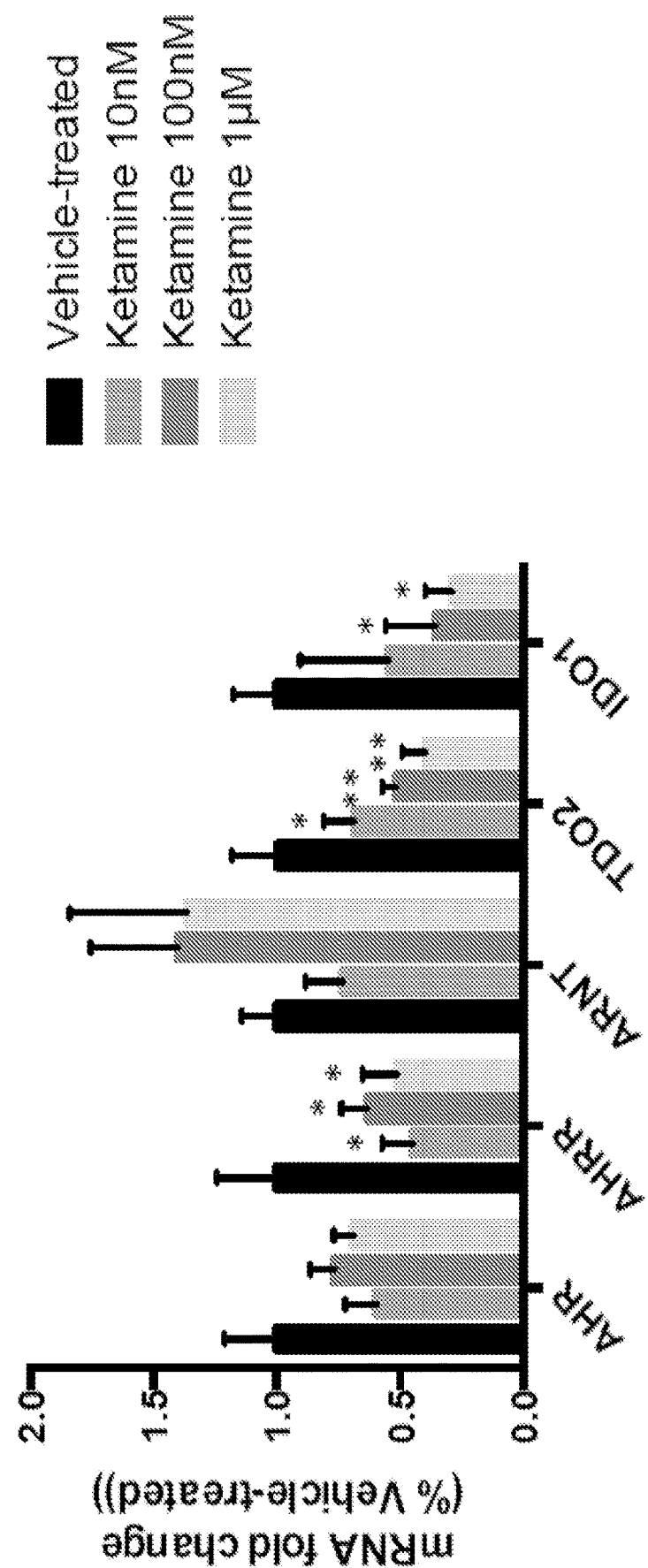
FIG. 8C is a graph plotting the change in mRNA levels for AHR, AHRR, ARNT, IDO1, and TDO2 after treatment of induced pluripotent stem cell (iPSC) neurons with vehicle or the indicated concentrations of ketamine.
Figure 9B:
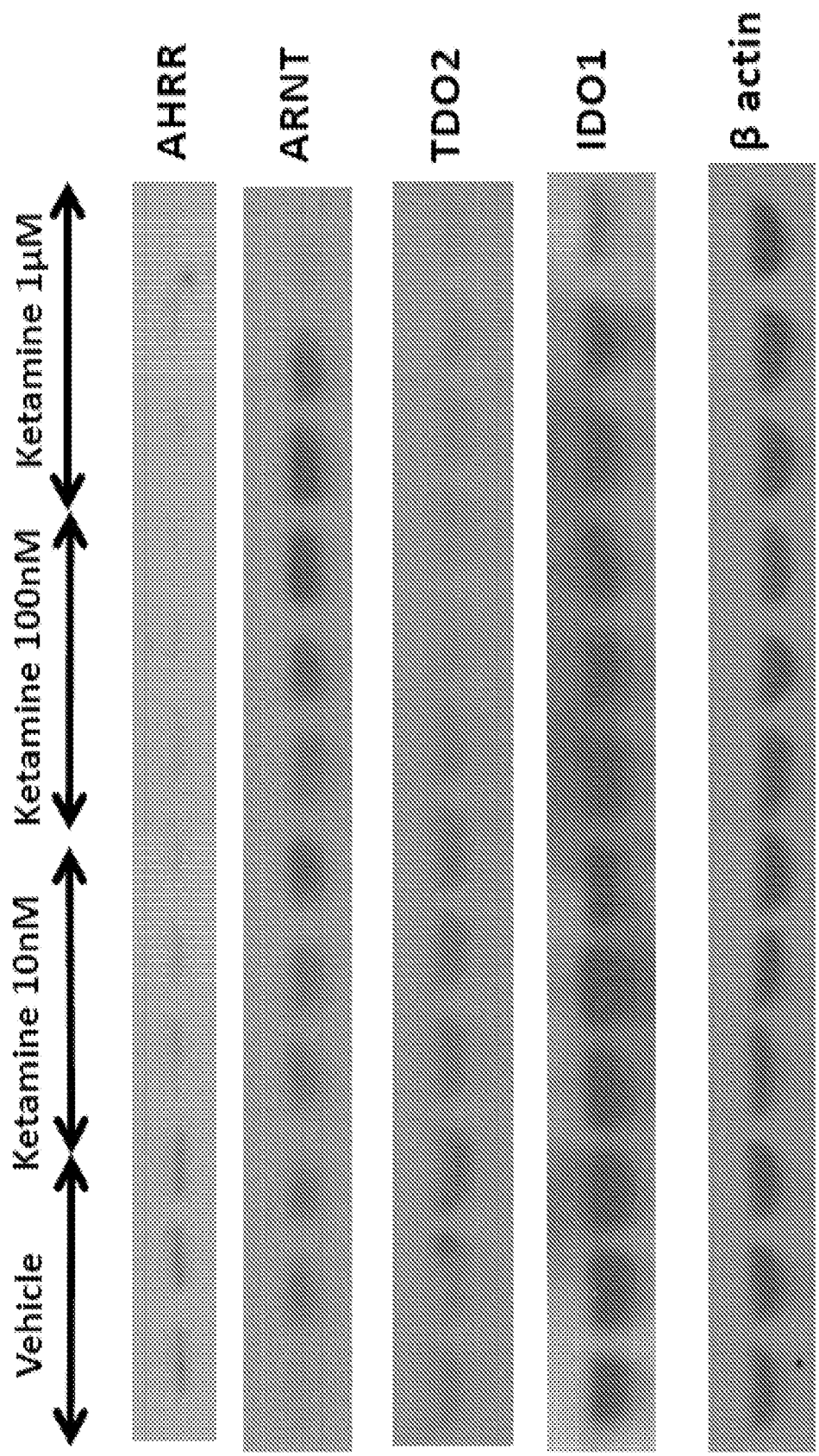
FIG. 9B is a picture of a Western blot showing AHRR, ANRT, TDO2, IDO1, and β-actin protein levels in lysates of iPSC neurons after treatment of the cells with vehicle or the indicated concentrations of ketamine.

Human glioblastoma cells (U251 and U87) were utilized for AHRR over-expression. AHRRΔ8 cDNA transfection in U251 cells resulted in a large increase in the mRNA levels of AHR and IDO1 (FIG. 7D). The mRNA levels of TDO2 also were significantly increased (FIG. 7D). mRNA levels for AHR, IDO1, and TDO2 reached a maximum induction within 8 hours after transfection, and gradually decreased by 48 hours, although significant elevation of the mRNA levels still was observed at 48 hours (FIG. 7D).

Example 6—Knocking Down of AHR, ARNT and Over-Expression of AHRR Increase AHRR Promoter Activity AHRR promoter activity was measured using a luciferase assay, showing that promoter activity was significantly increased in glioblastoma cells after knockdown of AHR and ARNT. AHRR promoter activity also was significantly increased in glioblastoma cells after AHRR overexpression, indicating that the AHRR protein can act as an inducer of its own transcription. Thus, knocking down AHR and ARNT can result in increased transcription of AHRR, which in turn, results in increased transcriptional activity of the AHRR promoter.

Example 7—AHR Genetic Variation is Associated with Increased AHRR, IDO1 and TDO2 Expressions in LCLs LCLs with v/v genotypic variants for AHR SNPs were observed to have increased expression of both mRNA and protein for AHRR, IDO1, and TDO2 versus wt/wt SNPs for AHR (FIG. 4), indicating the possibility of increased levels of KYN bio-synthesis in individuals carrying variant AHR alleles. Notably, the LCLs with v/v genotype for the AHR SNP (rs57791070) are associated with decreased expression of both AHR mRNA and protein.

Example 8—Effects of Ketamine in Cell Culture Models

Figure 10:
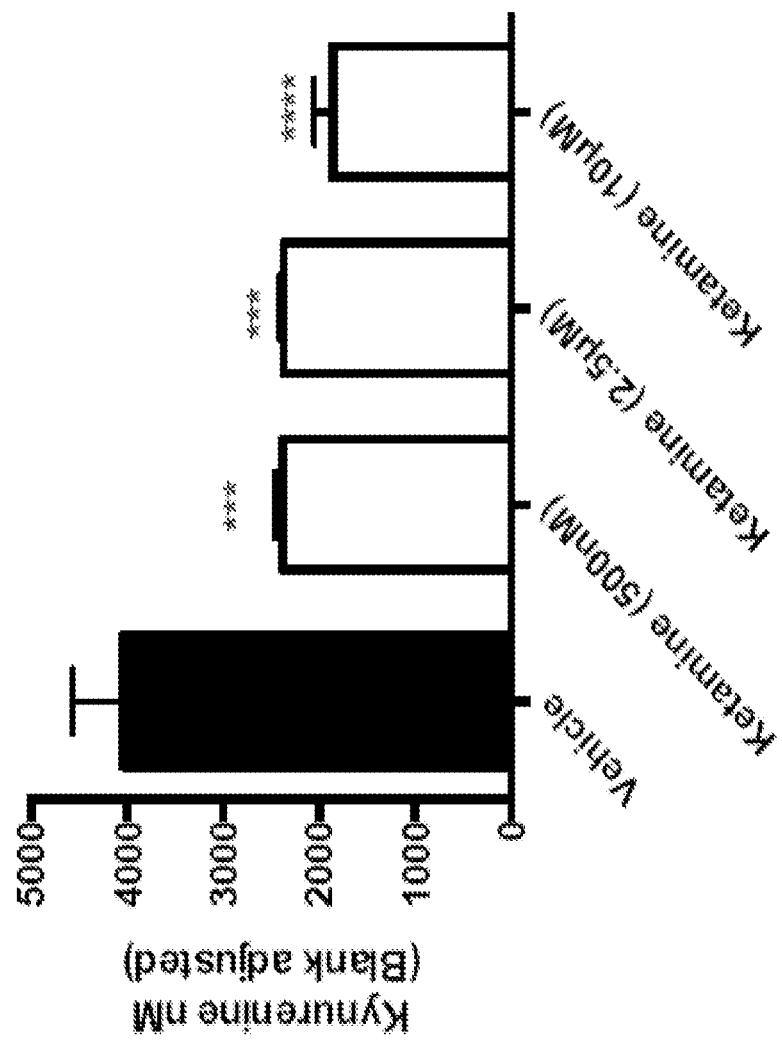
FIG. 10 is a graph plotting levels of secreted kynurenine in cell culture conditioned media samples from glioblastoma cells, after treatment of the cells with vehicle or the indicated concentrations of ketamine.

Ketamine was tested in cell culture-based models, including both glia (U251) and iPSC-derived neuron culture systems. Ketamine treatment resulted in decreased levels of both mRNA and protein for the rate-limiting enzymes of KYN biosynthesis, IDOL and TDO2 (FIGS. 8A, 8B, 8C, 9A, and 9B). Decreased levels of both mRNA and protein for AHRR also were observed after ketamine treatment. Further, measurement of secreted KYN in cell culture conditioned media samples of the glioblastoma cells revealed decreased levels after ketamine treatment (FIG. 10).

To date, monoamine neurotransmitter systems have been the primary target for antidepressant therapies. Recently, NMDA receptor-targeted strategies have been demonstrated to be of value in treating MDD. Both ketamine and another drug (GLYX13) act on NMDA receptors, and are now undergoing FDA review. However, drugs designed to modulate the AHR system are not under clinical trial for this purpose. The data presented herein are the first report of the unique properties of a drug (ketamine) in reducing KYN levels by acting on the AHR transcription factor system. These findings have potential significant implications for MDD therapy.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A pharmaceutical composition comprising a pharmaceutically acceptable carrier and a compound that is an AHR receptor agonist, and that does not bind to a glutamate receptor, wherein said compound is 3',4'-dimethoxy-α-naphthoflavone (DiMNF).

2. The pharmaceutical composition of claim 1, wherein administration of the compound to a cell results in increased levels of AHR and/or ARNT in the cell, decreased levels of AHRR in the cell, or both increased levels of AHR and/or ARNT and decreased levels of AHRR in the cell.

3. A method for treating a depression disorder in a subject, comprising administering to the subject a composition comprising a pharmaceutically acceptable carrier and a compound that is an AHR receptor agonist, and that does not bind to a glutamate receptor, wherein said compound is selected from the group consisting of 3-methyl cholanthrene; a halogenated-dibenzo-p-dioxin; 3',4'-dimethoxy-α-naphthoflavone (DiMNF); and 3,3'-Diindolylmethane (DIM).

4. The method of claim 3, wherein the depression disorder is MDD.

5. The method of claim 3, wherein administration of the composition to a cell results in increased levels of AHR and/or ARNT in the cell, decreased levels of AHRR in the cell, or both increased levels of AHR and/or ARNT and decreased levels of AHRR in the cell.

6. The method of claim 3, wherein the glutamate receptor is the NMDA receptor.

\* \* \* \* \*